(12) United States Patent
Gharavi

(10) Patent No.: US 6,429,023 B1
(45) Date of Patent: Aug. 6, 2002

(54) BIOSENSORS WITH POLYMERIC OPTICAL WAVEGUIDES

(75) Inventor: Alireza Gharavi, Chicago, IL (US)

(73) Assignee: Shayda Technologies, Inc., Chicago, IL (US)

( * ) Notice: Subject to any disclaimer, the term of this patent is extended or adjusted under 35 U.S.C. 154(b) by 0 days.

(21) Appl. No.: 09/357,204

(22) Filed: Jul. 20, 1999

Related U.S. Application Data
(60) Provisional application No. 60/093,473, filed on Jul. 20, 1998.

(51) Int. Cl.$^7$ .................................................. G01N 21/17
(52) U.S. Cl. ................... 436/167; 436/171; 422/82.11; 422/91; 356/478
(58) Field of Search .................. 422/82.11, 91; 436/164, 167, 171; 356/477, 478; 385/14, 142

(56) References Cited

U.S. PATENT DOCUMENTS

| | | |
|---|---|---|
| 4,608,344 A | 8/1986 | Carter et al. |
| 4,647,544 A | 3/1987 | Nicoli et al. |

(List continued on next page.)

FOREIGN PATENT DOCUMENTS

| | | |
|---|---|---|
| EP | 0 205 236 | 12/1986 |
| EP | 0 218 938 | 4/1987 |
| EP | 0 231 770 | 8/1987 |

(List continued on next page.)

OTHER PUBLICATIONS

Chen et al., "Two–Step Synthesis of Side–Chain Polyimides for Second–Order Nonlinear Optics," *Macromolecules*, 29 (2), 535–539 (1996).

(List continued on next page.)

*Primary Examiner*—Jeffrey Snay
(74) *Attorney, Agent, or Firm*—Marshall, Gerstein & Borun

(57) ABSTRACT

The present invention pertains to biosensors based on uniquely designed polymer optical waveguides that are adaptable to a variety of environments, and to both chemical and biological species. In particular, the invention relates to polymer-based, index of refraction-mediated analyte sensing devices.

22 Claims, 14 Drawing Sheets

U.S. PATENT DOCUMENTS

| | | |
|---|---|---|
| 4,671,938 A | 6/1987 | Cook |
| 4,717,508 A | 1/1988 | DeMartino |
| 4,720,355 A | 1/1988 | DeMartino |
| 4,746,186 A | 5/1988 | Nicia |
| 4,757,130 A | 7/1988 | DeMartino |
| 4,766,171 A | 8/1988 | DeMartino |
| 4,775,637 A | 10/1988 | Sutherland et al. |
| 4,795,664 A | 1/1989 | DeMartino |
| 4,815,843 A | 3/1989 | Tiefenthaler et al. |
| 4,838,634 A | 6/1989 | Bennion et al. |
| 4,851,502 A | 7/1989 | DeMartino |
| 4,855,376 A | 8/1989 | De Martino et al. |
| 4,857,273 A | 8/1989 | Stewart |
| 4,880,752 A | 11/1989 | Keck et al. |
| 4,887,884 A * | 12/1989 | Hayden ................. 252/585 |
| 4,898,691 A | 2/1990 | Borzo et al. |
| 4,932,738 A | 6/1990 | Haas et al. |
| 4,936,644 A | 6/1990 | Raskin et al. |
| 4,936,645 A | 6/1990 | Yoon et al. |
| 4,950,074 A | 8/1990 | Fabricius et al. |
| 4,978,476 A | 12/1990 | Allen et al. |
| 5,002,361 A | 3/1991 | DeMartino et al. |
| 5,006,285 A | 4/1991 | Thackara et al. |
| 5,007,696 A | 4/1991 | Thackara et al. |
| 5,039,186 A | 8/1991 | Man et al. |
| 5,044,725 A | 9/1991 | DeMartino et al. |
| 5,082,629 A | 1/1992 | Burgess, Jr. et al. |
| 5,093,883 A | 3/1992 | Yoon et al. |
| 5,100,589 A | 3/1992 | Ticknor |
| 5,106,211 A | 4/1992 | Chiang et al. |
| 5,135,876 A | 8/1992 | Andrade et al. |
| 5,156,810 A | 10/1992 | Ribi |
| 5,192,507 A | 3/1993 | Taylor et al. |
| 5,196,509 A | 3/1993 | Allen |
| 5,200,552 A | 4/1993 | Urano et al. |
| 5,202,231 A | 4/1993 | Drmanac et al. |
| 5,212,269 A | 5/1993 | Fischer et al. |
| 5,264,507 A | 11/1993 | Wiesenfeldt et al. |
| 5,274,061 A | 12/1993 | Urano et al. |
| 5,286,803 A | 2/1994 | Lindsay et al. |
| 5,298,588 A | 3/1994 | Gibbons et al. |
| 5,322,986 A | 6/1994 | Nutt |
| 5,340,715 A | 8/1994 | Slovacek et al. |
| 5,390,157 A * | 2/1995 | Revelli, Jr. ............ 369/112.27 |
| 5,393,645 A | 2/1995 | Etzbach et al. |
| 5,434,231 A | 7/1995 | Wiesenfeldt et al. |
| 5,459,232 A | 10/1995 | Sotoyama et al. |
| 5,461,131 A | 10/1995 | Wiesenfeldt et al. |
| 5,465,151 A | 11/1995 | Wybourne et al. |
| 5,484,821 A | 1/1996 | Mandal et al. |
| 5,496,700 A | 3/1996 | Ligler et al. |
| 5,496,701 A | 3/1996 | Pollard-Knight |
| 5,496,899 A | 3/1996 | Foll et al. |
| 5,534,201 A | 7/1996 | Summers et al. |
| RE35,407 E | 12/1996 | Wiesenfeldt et al. |
| 5,594,075 A | 1/1997 | Reinhardt et al. |
| 5,606,170 A | 2/1997 | Saaski et al. |
| 5,612,449 A | 3/1997 | Sotoyama et al. |
| 5,631,170 A | 5/1997 | Attridge |
| 5,659,010 A | 8/1997 | Sotoyama et al. |
| 5,663,308 A | 9/1997 | Gibbons et al. |
| 5,663,790 A | 9/1997 | Ekström et al. |
| 5,688,906 A | 11/1997 | Jen et al. |
| 5,712,705 A | 1/1998 | Fattinger et al. |
| 5,714,304 A | 2/1998 | Gibbons et al. |
| 5,736,592 A | 4/1998 | DeMeuse et al. |
| 5,738,806 A | 4/1998 | Beckmann et al. |
| 5,750,337 A | 5/1998 | Squirrell |
| 5,777,089 A | 7/1998 | Beckmann et al. |
| 5,781,677 A | 7/1998 | Jin et al. |
| 5,783,649 A | 7/1998 | Beckmann et al. |
| 5,837,804 A | 11/1998 | Yamagishi et al. |
| 5,846,814 A | 12/1998 | Galla et al. |
| 6,194,120 B1 * | 2/2001 | Chan et al. ............. 430/270.1 |

FOREIGN PATENT DOCUMENTS

| | | |
|---|---|---|
| EP | 0 238 789 | 9/1987 |
| EP | 0 290 061 | 11/1988 |
| EP | 0 297 530 | 1/1989 |
| EP | 0 337 405 | 10/1989 |
| EP | 0 351 832 | 1/1990 |
| EP | 0 372 433 | 6/1990 |
| EP | 0 380 139 | 8/1990 |
| EP | 0 394 027 | 10/1990 |
| EP | 0 396 172 | 11/1990 |
| EP | 0 406 888 | 1/1991 |
| EP | 0 413 903 A1 | 2/1991 |
| EP | 0 413 903 | 2/1991 |
| EP | 0 435 456 | 7/1991 |
| EP | 0 436 115 | 7/1991 |
| EP | 0 478 268 | 4/1992 |
| EP | 0 499 272 | 8/1992 |
| EP | 0 554 904 | 8/1993 |
| EP | 0 565 031 | 10/1993 |
| EP | 0 583 417 | 2/1994 |
| EP | 0 587 228 | 3/1994 |
| EP | 0 617 314 | 9/1994 |
| EP | 0 727 692 | 8/1996 |
| EP | 0 778 479 | 6/1997 |

OTHER PUBLICATIONS

Sotoyama, et al., "Directional–Coupled Optical Switch between Stacked Waveguide Layers Using Electro–Optic Polymer," *Japanese Journal of Applied Physics*, 31 (8B), L1180–L1181 (1992).

Yu et al., "Design and Synthesis of Functionalized Polyimides for Second–Order Nonlinear Optics," *Macromolecules*, 27(23), 6718–6721 (1994).

Yu et al., "A Generic Approach to Functionalizining Aromatic Polyimides for Second–Order Nonlinear Optics," *Macromolecules*, 28(3), 784–786 (1995).

EP 0 604 841 A1 published Jul. 6, 1994 and attached English language abstract (NERAC Abstract WNDABSM).

SPIE Proceedings Abstracts, "Nonlinear Optical Properties of Organic Materials VII", www.spie.org/web/abstracts/2200/2285.html, dated Dec. 13, 1999, Paper No. 2285–41 (p. 14), Paper No. 2285–47 (p. 16), Paper No. 2285–49 (p. 17), and Paper No. 2285–51 (p. 18).

* cited by examiner

Unmodified Chromophoric Polymer (UCP)

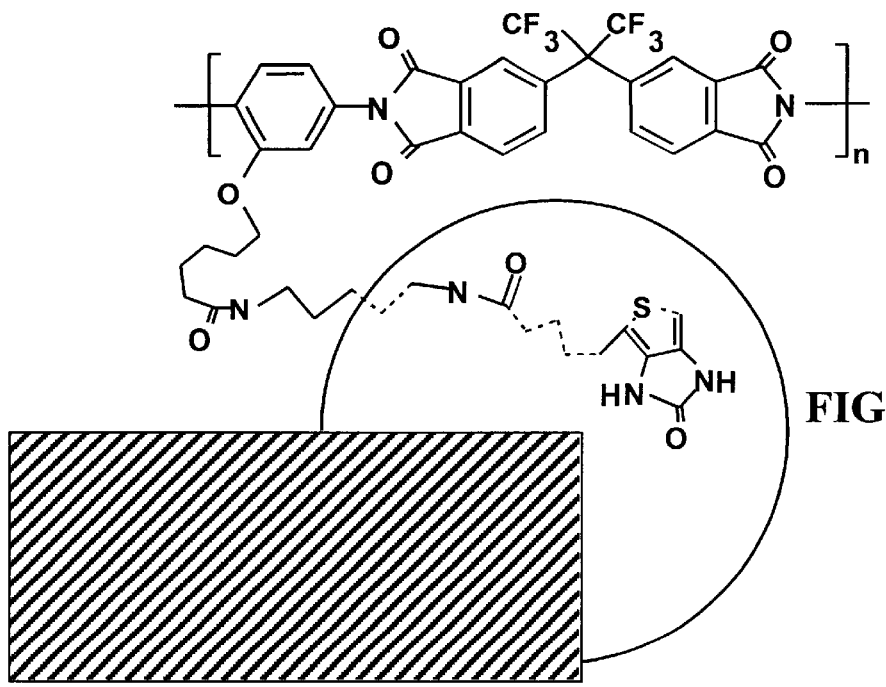
FIGURE 12C
FIGURE 13
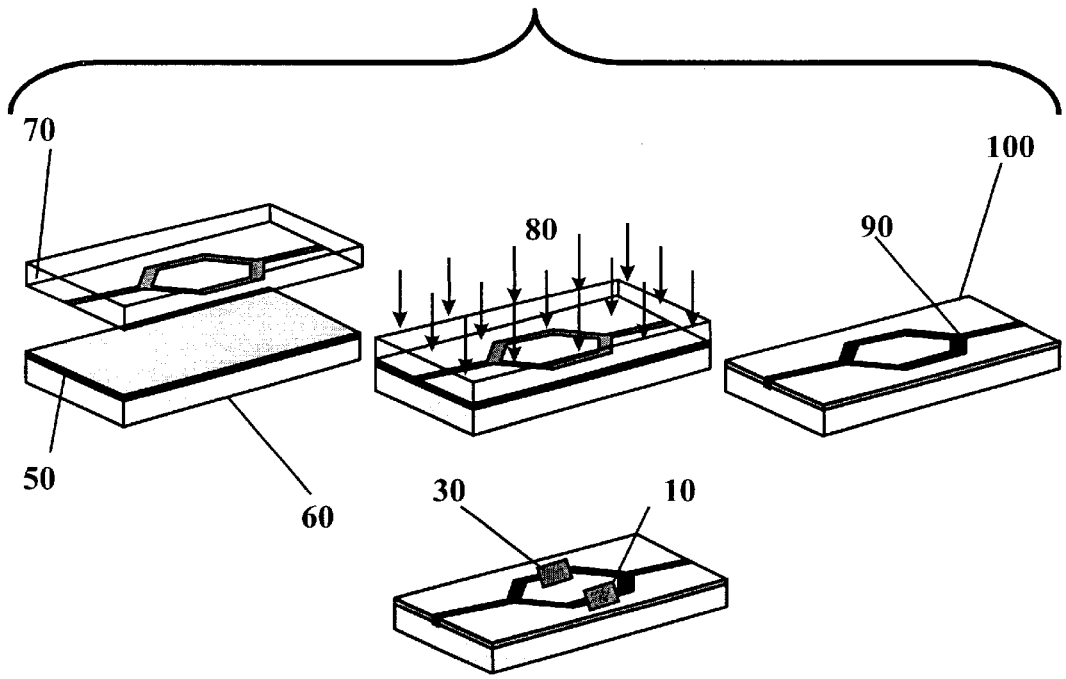

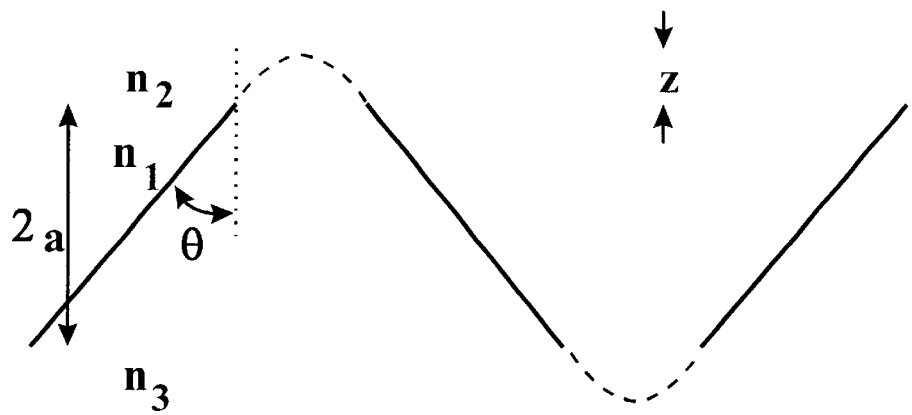
Ray Representation
FIGURE 14
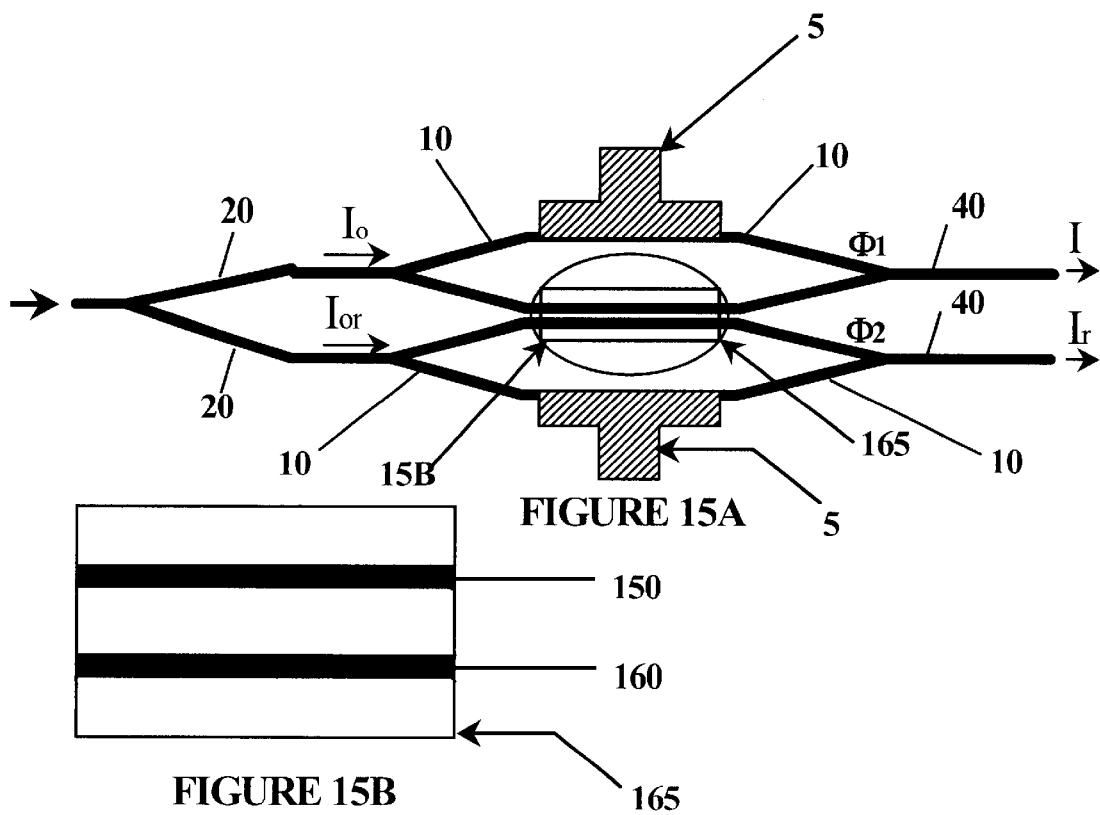
FIGURE 15A
FIGURE 15B

BIOSENSORS WITH POLYMERIC OPTICAL WAVEGUIDES

CROSS REFERENCE TO RELATED APPLICATIONS

This application claims the benefit of U.S. patent application Ser. No. 60/093,473, Jan. 20, 1998. +gi

GOVERNMENT RIGHTS IN THE INVENTION

The invention was made with Government support under Grant Number 1R43ES09477-01 from The Department of Health and Human Services (DHHS), Small Business Innovation Research Program, National Institute of Environmental Health Sciences. Accordingly, the government may have certain rights in the invention.

TECHNICAL FIELD OF THE INVENTION

The present invention pertains to biosensors based on uniquely designed polymer optical waveguides that are adaptable to a variety of environments, and to both chemical and biological species. In particular, the invention relates to polymer-based, index of refraction-mediated analyte sensing devices.

BACKGROUND OF THE INVENTION

Diagnostics is a rapidly growing field with medical, agricultural, environmental, and industrial markets. In the field of diagnostics, robust, low-cost, target-specific sensors play critical roles. In medicine, devices tailored to monitor for levels of substances in situ (e.g., sensing specific toxins, metabolites, etc., are of great value). In manufacturing or environmental contexts, such devices are employed for effluent monitoring, and in the detection of either inorganics or organics, to name but a few applications.

The potential of the market for specialty analytical technologies is suggested by an example from the health care industry, where a single category of diagnostic/testing devices—for monitoring glucose in diabetes management/self-management—is currently a $2 billion worldwide market, with an annual growth rate of 10–15% ("Business Review with Tom Hodgson", *Abbott World* (1997) 4–7). Other analytical demands, e.g., for the discrimination between each of the enantiomers in the preparation of a chiral pharmaceutical, have been clearly ordained, and have yet to have their full impact on the marketplace (Casy, *The Steric Factor in Medicinal Chemistry: Dissymmetric Probes of Pharmacological Receptors*, (New York: Plenum Press, 1993)). The need for analytical technologies underlies:

(1) the traditional and well-developed chromophore-, fluorophore-, etc. based methods (Blum et al., eds. Biosensor Principles and Application Bioprocess Technology, Vol. 15, (NY: Marcel Dekker, 1991); Rogers et al., eds. Biosensor and Chemical Sensor Technology, ACS Symposium Series 613 (Washington, D.C.: American Chemical Society, 1995); Mathewson et al., eds. *Biosensor Design and Application*, ACS Symposium Series 511 (Washington, D.C., American Chemical Society, 1992));

(2) more recent electrochemical efforts (including "receptor"-modified electrodes) (Blum et al., supra; Rogers et al, supra; Mathewson et al, supra); and (3) inroads into solid-state analyte sensing technologies (Blum et al, supra).

The limitations inherent to each of these methods have been given considerable attention in efforts to meet the demands of the diagnostic field (Katzir, ed. *Lasers and Optical Fibers in Medicine*, (NY: Academic, 1993) 204; McCurley et al., "Fiber-Optic Sensor for Salt Concentration Based on Polymer Swelling Coupled to Optical Displacement", *Anal. Chim. Acta.*, 249 (1991) 373–380). Medical diagnostic sensors which make use of fiberoptic components also have received increasing attention. Unfortunately, their inherent limitations—with respect to optode construction, calibration, sensitivity, chemical stability, response time, and dynamic range—have yet to be fully resolved (Katzir, supra; Rouhi, "Biosensors Send Mixed Signals", *C&EN*, (May 12, 1997) 41–45). As such, there is yet need for new analytical devices which address some or all of these shortcomings in prior devices.

The sensing devices of almost all common electronic and photonic instruments are currently based on inorganic materials, including biosensors (e.g., the inorganic fiber-optic- and silicon-based Mach-Zehnder interferometer) ("Laser Focus World", (December 1996) 66). However, more recently, organic non-polymeric and polymeric materials have begun to emerge as potential chemical systems suitable for discrete sensing. In the 1990's, polymeric-based interferometer and other devices generated great interest (Girton et al., "Electrooptic Polymer Mach-Zehnder Modulator", In ACS Symposium Series 601, *Polymers for Second Order Nonlinear Optics* (Washington, D.C., 1995) 456–468). The organic polymeric materials exhibit physical and chemical "flexibility", and, for instance, can be relatively easily chemically modified to suit specific applications. This flexibility eases their fabrication (e.g., into integrated optical circuitry) which contributes to lower costs of manufacture. The flexibility promotes rapid cycles of material design, preparation, testing, and redesign. Polymer-based devices could ultimately be mass-produced using simple printing processes. Moreover, organic polymers provide a large inventory of photonic materials that have a low dielectric constant. Certain of the polymers show high stability and optical nonlinearity.

Polymeric materials have more recently emerged as materials for use in optical applications (Keil, "Realization of IO-Polymer-components and Present State in Polymer Technology", In *Integrated Optics and Micro-Optics with Polymers*, (Stuttgart-Leipzig: B. G. Teubner Verlagsgesellschaft, 1993) 273; Ito et al., eds. *Polymeric Materials for Microelectronic Applications*, ACS Symposium Series 579 (Washington, D.C.: American Chemical Society, 199); Lindsay et al., eds., *Polymers for Second Order Nonlinear Optics*, ACS Symposium Series 601 (Wash., D.C.: American Chemical Society, 1995) pp. 1, 111, 130, 158, 172, 347, 381; Edelman et al., eds. *Biosensors and Chemical Sensors*, ACS Symposium Series 487 (Wash., D.C.: American Chemical Society, 1992)). The tremendous excitement in industry regarding these new materials suggests polymeric materials will survive to compete with well established and low cost inorganic materials. (Levenson et al., "Advances in Organic Polymer-Based Optoelectronics" In ACS Symposium Series 601, *Polymers for Second Order Nonlinear Optics*, G. A. Lindsay and K. D. Singer, eds., (Washington, D.C.: American Chemical Society, 1995)).

Among the more recently developed polymeric materials are polyimides that have been demonstrated to have superior optical and physical characteristics. In particular, certain polyimides show thermal stability, as well as high optical nonlinearity (as reflected in their $r_{33}$ values) (Lindsay et al., supra). W. R. Seitz, commenting on related work from the 1980's, noted the potential for "rugged and inexpensive" sensors based on devices which monitor the change in the index of refraction on transmission of light through such an optical component (McCurley et al., supra). Traditionally, Seitz notes, such applications have been limited by a lack of selectivity, leading once again to reliance upon the optical properties of the analyte per se.

The present invention accordingly seeks to overcome these deficiencies in the prior art by providing a novel class of waveguide sensors that employ a variant of a recently developed polyimide polymers that is uniquely engineered to allow modification by recognition elements (i.e., concurrent with or following device fabrication). The recognition element-analyte tests provided by the sensors can accommodate a range of analytes (e.g., inorganic and organic, polar and apolar, low and high molecular weight). These and other objects and advantages of the present invention, as well as additional inventive features, will be apparent from the following description of the invention provided herein.

BRIEF SUMMARY OF THE INVENTION

The present invention provides inter alia biosensors that are based on uniquely designed polymer optical waveguides that are adaptable to a variety of environments, and to both chemical and biological species. In particular, the invention provides polymer-based, index of refraction-mediated analyte sensing devices.

BRIEF DESCRIPTION OF THE FIGURES

FIGS. 12A–C are schematic representations of modifications to the MMP polymer—i.e., cryptand-modified polymer (A), β-cyclodextrin-modified polymer (B), and glucose-oxidase-(avidin-biotin)-modified polymer (C). Symbols: circle, avidin; box, glucose oxidase.

FIG. 13 shows photobleaching steps for waveguide fabrication. Symbols: 10, modulator arm; 30, sensor arm; 50, 2°-NLO polymeric material; 60, solid support; 70 metallic mask (e.g., quartz mask); 80, irradiation; 90, unbleached waveguide; 100, bleached polymeric material.

FIG. 14 is a schematic representation of an evanescent wave in a waveguide of the invention, where $n_1$, $n_2$, and $n_3$ are the refractive indices of each layer, θ is the incident internal angle, 2a is the polymer waveguide thickness, and z is the penetration depth.

FIGS. 15A–B are schematic representations (as seen from the top) of a double Mach-Zehnder interferometer including waveguide and electrode layouts, with FIG. 15B showing an expanded version of the sensor area depicted in FIG. 15A. Symbols: 5, electrode (i.e., bottom and top); 10, modulator arm; 20, input; 30, sensor arm; 40, output; 140, sensor area; 150, bio-activated arm; 160, reference arm; 165, sensor area; intensity of optical output of the bioactivated arm and modulator arm; $I_o$ and $I_{o'}$, I, intensity of the optical input to the interferometer; $I_r$, intensity of optical output of the reference arm and modulator arm; $\phi_1$ and $\phi_2$, optical phases of the wavefronts at the combining point.

Figure 1:
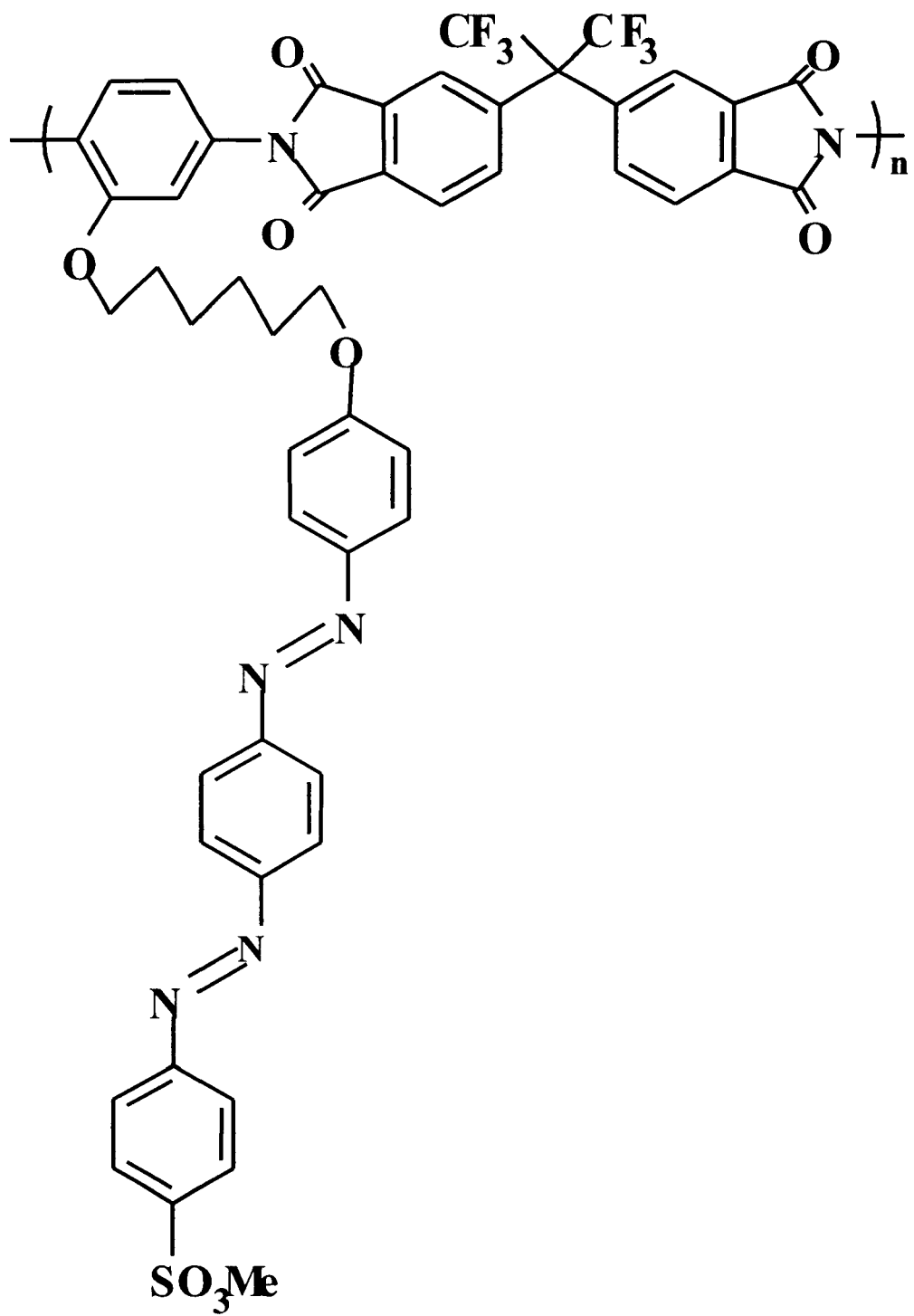
FIG. 1 depicts the chemical structure of polyimide-alkoxy sulfone diazo. Symbol: n, ranging from about 44 to about 600.

100, bleached polymeric material; 170, modified 2°-NLO polymer; 180, cladding; 190, bottom electrode.

DETAILED DESCRIPTION OF THE INVENTION

The present invention provides a family of waveguide sensing devices comprised of optical nonlinear second-order polymers. This is a novel and unexpected use of such polymers, as explained below.

The phase of light propagating through a waveguide or other optical device is sensitive to changes in the refractive index of the device. Structural perturbation of the waveguide's interior—or, indirectly, of the surface via evanescent waves (Katzir, supra; Mathewson et al., supra, pp. 179)—affect light propagation, which is confirmed by a change in the index of refraction (Gharavi et al., "Fine-Tuning Optical Nonlinearity and Thermal Stability in Functionalized Co-Polyimides", American Physical Society, Mtg. Abstr., Mar. 18–22, 1996, St. Louis, Mo.). The present invention accordingly provides for modifications to a waveguide's polymer structure which engineer in specific surface functional groups having ability to facilitate perturbation of the evanescent wave, and so to register as changes in the propagated light. This novel and unexpected use of optical nonlinear second-order polymers allows waveguide devices such as interferometers to be made into sensors which directly convert these changes into optical signals. Further modifications to the waveguide's structure which engineer specific functions—such as molecular recognition or catalytic elements functioning as analyte binding partners—have the potential to allow detection of specific analytes (e.g., selective detection of metal ions, and drug and metabolite enantiomers, etc). Such specific functionalization (i.e., modification) according to the invention allows simple, polymer-based devices to function as electrooptic sensors, with characteristics of sensitivity limited only by the association chemistry of the analyte binding partner pair, as further described below. In view of this, the present invention provides a family of biosensors based on uniquely designed polymer waveguides that are adaptable to a variety of environments, and to both chemical and biological species. More specifically, the invention preferably provides a polymer-based, index of refraction-mediated analyte sensing device.

In particular, the invention provides a waveguide sensing device that preferably comprises:

(a) an input port;

(b) a modulator arm;

(c) a sensor arm;

(d) an output port; and (d) a detector,

DEFINITIONS

Certain standard terms are employed in describing the invention. Illustrative definitions of these terms are set out below, and in the Examples which follow. Should there be any term that is left undefined, or any possible ambiguity in the meaning of a term, the broadest possible definition known in the optics/electronics fields that is consistent with the scope and goals of the invention is to be applied. Also, like numbering is used for the same components in each of the Figures and in the descriptive text.

A second-order nonlinear optical (2°-NLO) polymer is a polymer that is optically active—i.e., its index of refraction changes due to an applied electric field, and the change is proportional to the square of the applied electric field. Preferably according to the invention, a 2°-NLO polymer is obtained by the incorporation into a polymer backbone of a chromophore having 2°-NLO characteristics, and/or which exhibits those characteristics when present in the polymer backbone.

A "waveguide" is an entity of material boundaries or structures for guiding electromagnetic waves. More specifically, a waveguide is an optical waveguide, or any structure capable of guiding optical power (i.e., carrying one or more optical signals). A "device" preferably includes any single preferred entity as set forth herein (e.g., including, in particular, a waveguide), or any combination of elements (e.g., a combination of a waveguide and an input port, a modulator arm, a sensor arm, an output port, a detector, and the like) either alone, or, in a higher level of organization (e.g., present in a system or subsystem such as a board or motherboard). Preferably these entities are employed in optical systems, although each may exist in any combination, or independently (e.g., a hand-held device), or as part of a system that is other than predominantly optical (i.e., a mix of optical and nonoptical systems). The expression "optical system" as used herein refers to any system which employs (i.e., at some level) optical signals to convey information across an optical waveguide medium.

Desirably a device according to the invention is optically active, although optically inactive devices could be employed according to the invention (e.g., devices that do not include a 2°-NLO chromophore). However, one unifying feature of all the optically active devices of the invention is their incorporation of a 2°-NLO polymer, or a polymer having the desirable properties set forth herein, as further described below. A "sensing device" is a device that can be employed to detect (i.e., qualitatively or quantitatively) a particular analyte. In particular, preferably a device according to the invention minimally includes an interferometer that comprises a 2°-NLO polymer.

To function as a waveguide, the index of refraction in any layer surrounding the waveguide must be less than the index of refraction in the waveguide itself. This difference in refractive index between the waveguide itself and any adjacent layer (i.e., "$\Delta n$" in Example 5) preferably is equal to or greater than 0.001, and desirably is no more than 0.1. However, with alternate thicknesses of waveguide, it is conceivable that the range of differences may be slightly broader. Such alternates are contemplated by the present invention.

Thus, desirably the present invention contemplates an "asymmetric waveguide" and a "symmetric waveguide". In the case of an asymmetric waveguide, i.e., comprised of a waveguide surrounded by an upper and lower layer, the refractive indices of the upper and lower layers are not equal to each other, and are less than the refractive index of the waveguide. In the case of a symmetric waveguide, i.e., comprised of a waveguide surrounded by an upper and lower layer, the refractive indices of the upper and lower layers are equal to each other, and are less than the refractive index of the waveguide. This is further described in Example 5.

An "interferometer" is an instrument that employs the interference of light waves for purposes of measurement. Any of the devices, systems, or subsystems according to the invention further preferably can incorporate or comprise an interferometer, as well as other optional components. Preferably an interferometer according to the invention is a Mach-Zehnder interferometer.

According to the invention, an electric field is generated with any appropriate power source (e.g., AC or DC power source), and communicated to the device by means of electrodes (i.e., an electrode contacting either side of the modulator arm so as to create an electric field therein). The electrodes used in the present invention preferably is made of at least one of the following materials: metals such as gold, silver, platinum, copper, and alloys; conductive materials such carbon black, conductive epoxy. However, any electrode having the ability to conduct charge and capable of functioning as an "electrode" as that term is understood in the art can be employed in the methods and devices of the invention. Generally, an electrode need only supply a small amount of voltage, e.g., from 0 to about 50 volts, although in certain applications, it may be preferable to employ a higher voltage. For supplying voltage to an invention, generally, the polymer waveguide needs to be contacted by both an upper and a lower electrode such as is known in the art.

According to the invention, an "analyte" is any entity present in a sample according to the invention whose presence and/or amount is of interest. An analyte thus desirably includes, but is not limited to: an ion (e.g., lead); an organic (e.g., phenols, carboxylates, and the like); a drug (e.g., tryptamines, hydantoins, barbitals, and the like); a substrate for a particular enzyme which can be detected by an enzyme bound to avidin, which itself is bound to the biotinylated device (e.g., glucose can be detected by glucose oxidase).

Preferably, a sample is any sample of interest in which an analyte might conceivably be contained. For instance, a "sample" desirably is any sample isolated from nature (e.g., including but not limited to a soil, air, water, or bodily sample), or is a sample that, for instance, is synthesized in a laboratory. To facilitate contacting the sensing device of the invention, desirably a sample is in a form that can be distributed (e.g., dissolved) in an appropriate solvent. Thus, accordingly, a sample can be a solid, liquid, or gas. Preferably, when assessed using the sensing device of the invention, the sample is distributed in a solvent (i.e., a liquid solvent), and thus is applied to the sensing device in liquid form. Desirably the sensing device is immersed in the solvent containing the sample (or, for a control, in the solvent itself). For this to be accomplished, preferably all components of the device other than the sensor arm are appropriately housed or contained such that they do not actually contact the sample. Alternately, preferably the sample is merely applied directly to the sensor arm(s) (or sensor area) of the device. Some processing of the sample might be necessary prior to its application to the device. Such processing is dictated by the particular analyte to be detected, and its optimization is well within the ordinary skill of the researcher.

An "analyte binding partner" is any entity capable of binding (and preferably, specifically binding) an analyte. The analyte preferably binds with the analyte binding partner to form a so-called "analyte-binding partner pair". Preferably an analyte binding partner is a receptor for the analyte (e.g., as the term "receptor" is commonly understood in the art), a molecular recognition element (e.g., an agent or moiety that specifically recognizes an analyte), or a catalytic element (e.g., an agent or moiety that catalyzes conversion of a substrate analyte to product), and an enzymic element (e.g., an enzyme that drives reaction of a substrate analyte to product). An analyte according to the invention also preferably can be either an antibody (e.g., as where an antigen is the analyte-binding partner, e.g., by covalent association with the polymer waveguide) or an antigen (e.g., as where an antibody is the analyte-binding partner, e.g., by its specific recognition of the tether region, or other region of the polymer waveguide). Desirably, specific analyte binding partners employed according to the invention are selected for their characteristics in waveguide sensing of particular analytes. The preferred analyte binding partners include, but are not limited to those that provide: (1) ion-selective detection (e.g., of $Pb^{2+}$); (2) enantioselective sensing of a drug (e.g., mephobarbital); (3) detection of a binding protein by its ligand (e.g., avidin by biotin); and (4) an enzyme product, inhibitor and substrate (e.g., by glucose oxidase). Such analyte-binding partner pairs further desirably include any immobilizable host/guest or receptor/catalyst interaction, or other interaction. Such waveguide sensing according to the invention can be employed in any of a variety of fields (e.g., medical, environmental, manufacturing, etc.) where analyte interaction chemistries are available, and where it is desirable to assess or quantitate an analyte.

According to the invention, a "sensor" or "sensor arm" is the site of analyte addition, i.e., the arm of the interferometer to which analyte is applied. A "modulator" or "modulator arm" is another arm of the interferometer, which is not contacted by analyte. According to the invention, preferably the modulator arm is contacted by at least two electrodes arranged in such a fashion as to create an electric field at the modulator arm. An "input port" is a tube or channel that supplies optical signal to the interferometer. The optical signal supplied through the input port is dependent on the particular structure of the waveguide, i.e., the absorption spectrum of the particular 2°-NLO chromophore incorporated into the polymer structure of the waveguide, as further discussed below. An "output port" is a tube or channel that receives optical signal from the interferometer, and communicates it to a detector. A "detector" is a device that translates an optical signal into electrical signal (i.e., is a light detector, such as preferably, a photodiode).

According to the invention, a waveguide is comprised of a layer of 2°-NLO polymer. Desirably the waveguide is surrounded by cladding (e.g., a glass or plastic coating) and/or a support for the NLO polymer. The cladding can include one or more layers of 2°-NLO polymer, or other material and further can include a buffer (e.g., as set out in FIG. 5). According to the invention, "a buffer" is an optical buffer, i.e., a medium that does not exhibit optical activity or optical nonlinearity It is necessary for proper functioning of the waveguide, however, that the index of refraction in any layer surrounding the waveguide is less than the index of refraction in the waveguide itself. The index of refraction in each layer is impacted by the chromophore concentration, the nature of the chromrophore, and the nature of the polymer backbone. Of course, these parameters can easily be optimized by one skilled in the art. Desirably, the waveguide can comprise any part of a circuit or optical device.

Figure 5:
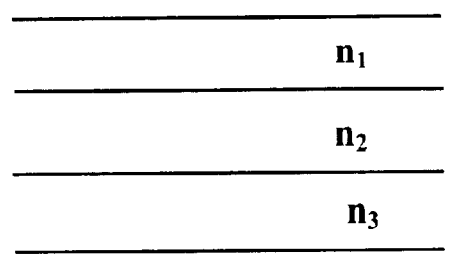
FIG. 5 is a diagram of a buffered waveguide and the corresponding differing refractive indices $n_1$, $n_2$, and $n_3$, that define each layer.

A device according to the invention can comprise one or more polymer layers as depicted in FIG. 5. FIG. 5 diagrams a waveguide where the refractive indices $n_1$, $n_2$, and $n_3$, are all different. The layers having these respective indices can comprise either air, buffer, and/or 2°-NLO. A "buffer" can be another polymer or any other material which: (1) has a lower refractive index than the guiding layer and light of the relevant range (i.e., range of chromophore excitation of chromophore employed in the device) passes through unaffected, (2) is employed to separate one layer from another layer or material (e.g., electrode), and (3) is noninterfering with the optical properties of layers above and/or below the buffer layer. Thus, a buffer layer can act merely as a separator and can be, for instance, a polymer such as polyimide, where the polymer (polyimide) does not contain any chromophor. In particular, preferably the buffer is polyimide, PMMA, or polystyrene that does not contain a chromophor.

2°-NLO Chromophores and Resulting 2°-NLO Polymers

A critical feature of the sensing devices of the invention is that they all contain 2°-NLOs polymers. As previously described, these 2°-NLOs polymers generally derive their second order optical nonlinearity from chromophores included in the structure of the polymer.

Preferably the 2°-NLOs employed in the invention (or other appropriate polymer having comparable properties to 2°-NLOs) exhibit thermal and mechanical stability, and high optical non-linearity. Desirably the 2°-NLO does not suffer thermnal decomposition until above about 300° C. Optimally the 2°-NLO has a large electro-optic coefficient ($r_{33}$) ranging anywhere from between about 5 to about 40 picometer/volt (e.g., as reported in the literature).

It particularly is preferred according to the invention that the 2°-NLO is a polyimide, i.e., having as a polymer "backbone" poly [N, N (1,4 phenylene)-4,4'(hexa fluoroisopropylidene) diphthalic imide] depicted as "Z" in Structure I below and hereafter referred to generally as "polyimide" (although "S" and "C" present in the polyimide may differ, and are further described below):

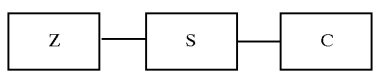
Structure I

In Structure I, the preferred structure of the 2°-NLO polymer according to the invention, the polymer backbone is attached to a spacer, "S", which itself is attached to a chromophore "C", each of which is further described below. The polyimide according to the invention optionally can be modified or substituted if beneficial for a particular application, so long as such modification/substitution allows functionality within the spirit and scope of the invention (e.g., does not substantially negate the optical neutrality of the polyimide).

In situations where it is not necessary that the polymer backbone exhibit thermal stability above 300° C., the polymer backbone can comprise the following polymers (or other polymers) instead of polyimide, and which have the glass transition values (° C.) indicated: Poly(methyl methacrylate), 114; Polystyrene, 100; Poly(p-hydroxystyrene), 150; Polycarbonate, 150; Polyester, 38–130; Polyurethane, 140; Poly(phenylene vinylene), 40; Polyquinoline, 175; Polyamide, 276; Polyimide, 310. Thus, desirably according to the invention, these other polymers can be employed instead of polyimide as the polymer backbone "Z".

In particular, however, preferably the polymer backbone "Z" is polyimide, i.e., having Structure II ($M_w$ of about 454) depicted below:

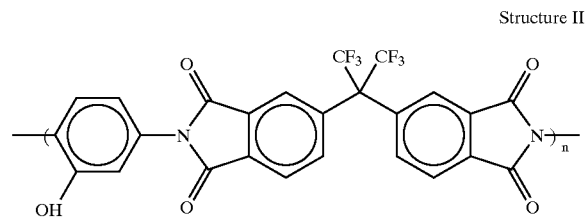
Structure II where n preferably is any number ranging from about 44 to about 600, and desirably ranges from about 100 to about 300. Generally it is found that longer chains (i.e., where n is greater than 44) give better properties in the sense that the chains intertangle better. Too great of a chain length, however, deleteriously impacts polymer solubility.

It further is desirable according to the invention that the polymer backbone "Z" is a polyamic acid having Structure III depicted below, and which upon heating becomes insoluble in organic solvents:

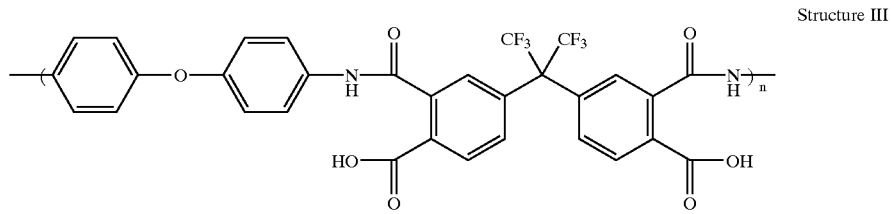
Structure III where n preferably is any number ranging from about 44 to about 600, and desirably ranges from about 100 to about 300.

The spacer, "S", in Structure I preferably is a chain of from 0 to about 30 carbons (or other moieties such as a carbon chain substituted with oxygen, nitrogen, or other appropriate moiety, or that optionally includes one or more double or triple bonds). The spacer desirably provides optimal spacing such that the polymer backbone is appropriately attached to, and does not interfere with, the functionality of the chromophore ("C"). In particular, preferably the spacer preferably has a length of from about 1 to about 10 atoms, and even more desirably, from about 2 to about 6 atoms. However, the spacer must be of sufficient length and character such that it does not interfere with the function of (e.g., the conjugation of) the attached chromophore, as well as does not interfere with the 2°-NLO properties of the polymer. A preferred spacer according to the invention is oxytrimethylene spacer.

With regard to the chromophore, "C," the 2°-NLOs polyimide with chemically attached (i.e., polyimide-alkoxy sulfone diazo, depicted in FIG. 1) or doped sulfone diazo (Mordant Orange 10, purchased from Sigma-Aldrich Fine Chemicals, St. Louis, Mo.) chromophore, polyimide-dialkylamino nitro azo (depicted in FIG. 2), and polyimide-dialkyl amino nitro diazo (depicted in FIG. 3; see, Saaedeh et al., "Polyimides with a Diazo Chromophore Exhibiting High Thermal Stability and Large Electrooptic Coefficients", *Macromolecules*, 30 (18), 5403–5407 (1997); Yu et al., "Novel Second-Order Nonlinear Optical, Aromatic and Aliphatic Polyimides Exhibiting High-Temperature Stability", *Applied Physics Letters*, 66, 1050–1052 (1995); Yu et al., "Novel Second-Order Nonlinear Optical Polyimides," *Society of Photooptical Instrumentation Engineers*, 2527, 127–136) are especially preferred for use in the invention. These polyimides incorporate the chromophores dialkyl amino nitro azo (e.g., present in polyimide-dialkyl amino nitro azo), sulfone diazo (e.g., present in polyimide-sulfone diazo), and dialkyl amino nitro diazo (e.g., present in polyimide-dialkyl amino nitro diazo). These polyimides (as well as other polyimides, or other polymers appropriate for optical applications) optimally can be modified by the incorporation of different chromophores into the polyimide backbone, allowing the responsiveness of the 2°-NLO to different wavelengths of light to differ. Also especially preferred is the polymer polyimide-alkoxy sulfone stilbene depicted in FIG. 9.

Such modification of the polyimide backbone with different chromophores is known in the art, and is described, for instance, in Marder et al., *Nature*, 388, 845–851 (1997). The chromophore incorporated in the polyimide can be any chromophore, but desirably is a chromophore including, but not limited to: (a) the three chromophores previously described, and (b) those chromophores depicted in Table 1. In Table I below, "$\mu$" is the dipolar moment of the molecule, "$\beta$" is the hyperpolarizability, and "$\lambda$" is the wavelength.

TABLE 1

| | Structure | $\mu\beta \times 10^{48}$ (esu) | $\lambda_{max}$ (nm) |
|---|---|---|---|
| 1 | $H_2N$—⬡—CH=CH—⬡—$SO_2CH_3$ | — | 390 |
| 2 | $MeO$—⬡—CH=CH—⬡—$NO_2$ | — | 356 |
| 3 | $H_2N$—⬡—CH=CH—⬡—$NO_2$ | — | 402 |
| 4 | $NMe_2$—⬡—(CH=CH)$_n$—⬡—$NO_2$   n = 2 to 4 | 813 (n=2)<br>1074 (n=3)<br>1700 (n=4) | 442<br>458<br>464 |
| 5 | $Me_2N$—⬡—N=N—⬡—$NO_2$ | 751 | 480 |
| 7 | $NPh_2N$—⬡—N=N—⬡—$NO_2$ | 788 | 486 |
| 8 | $Et_2N$—⬡—N=N—⬡—$NO_2$ | 996 | 494 |

TABLE 1-continued

| | Structure | $\mu\beta \times 10^{48}$ (esu) | $\lambda_{max}$ (nm) |
|---|---|---|---|
| 9 | 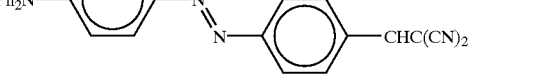 | 1360 | 526 |
| 10 | 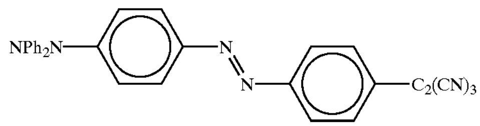 | 2776 | 602 |
| 11 | 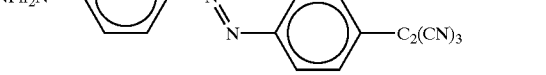 | 19000 | 504 |
| 12 | 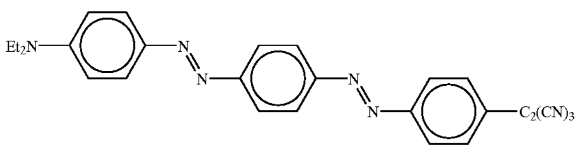 | 24000 | — |
| 13 | 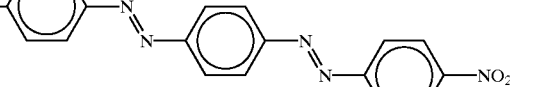 | 276 | 362 |
| 14 | 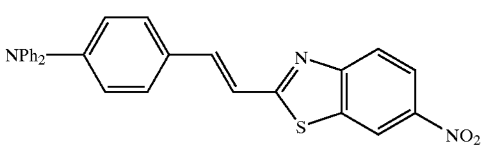 | 756 | 458 |
| 15 | 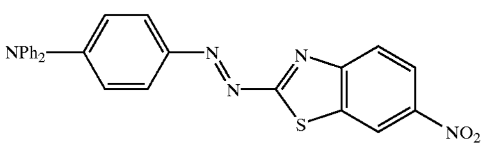 | 1390 | 550 |

Desirably the chromophore employed in the invention has an absorption wavelength from between about 200 nm and about 800 nm, preferably from between about 300 nm and about 600 nm. The preferred chromophores according to the invention also desirably have an effective cis-trans isomerization process when excited at their absorption wavelengths. Also, desirably the chromophores are such that polarization alone can be used to induce alignment in the chromophores (e.g., as described in Rochon et al., "Optically Induced and Erased Birefringence and Dichroism in Azoaromatic Polymers", Appl. Phys. Lett. 60, pages 4–5 (1992); Kim et al., "Laser Induced Holographic Surface Relief gratings on Nonlinear Optical Polymer Films", Appl. Phys. Lett. 66, pages 1166–1168, (1995)). Optimally this induced alignment will be in the direction to reduce interaction with the incident polarized light.

Figure 2:
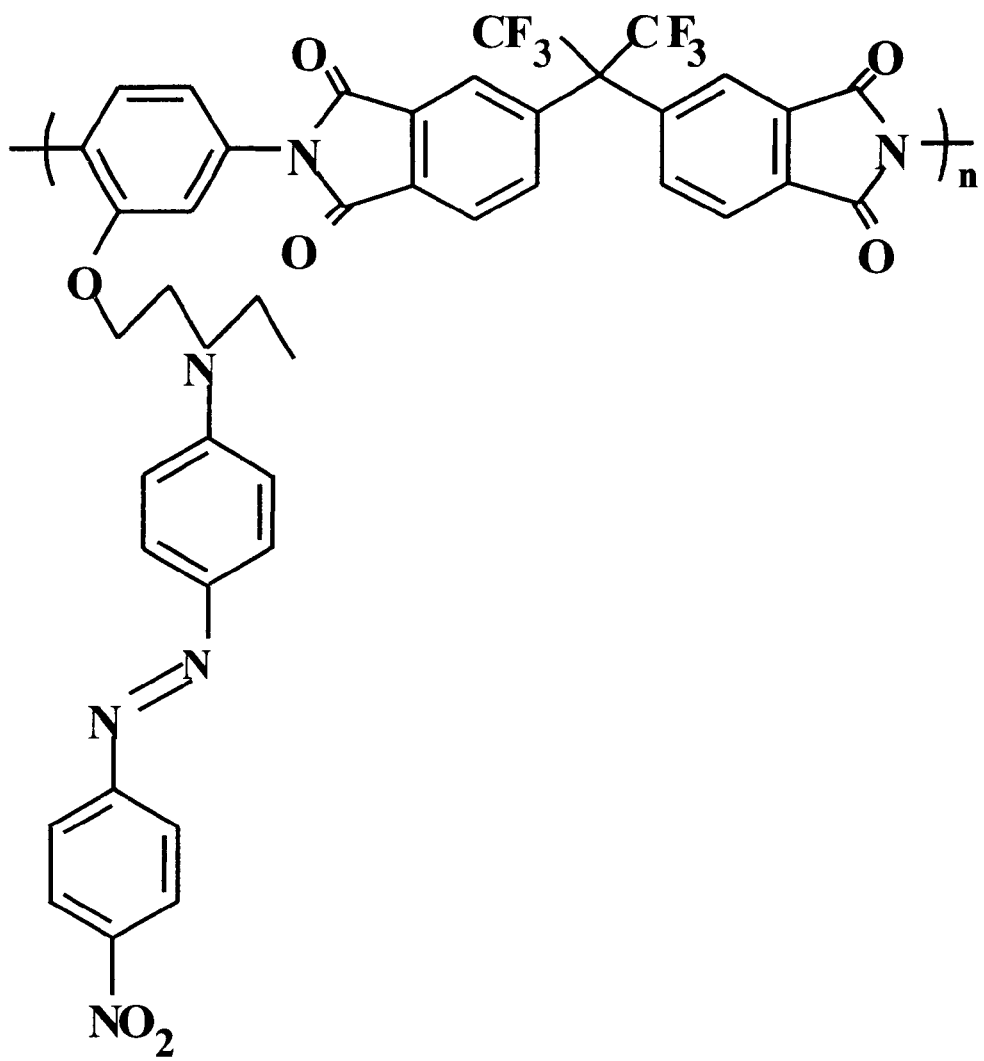
FIG. 2 depicts the chemical structure of polyimide-dialkyl amino nitro azo. Symbol: n, ranging from about 44 to about 600.
Figure 3:
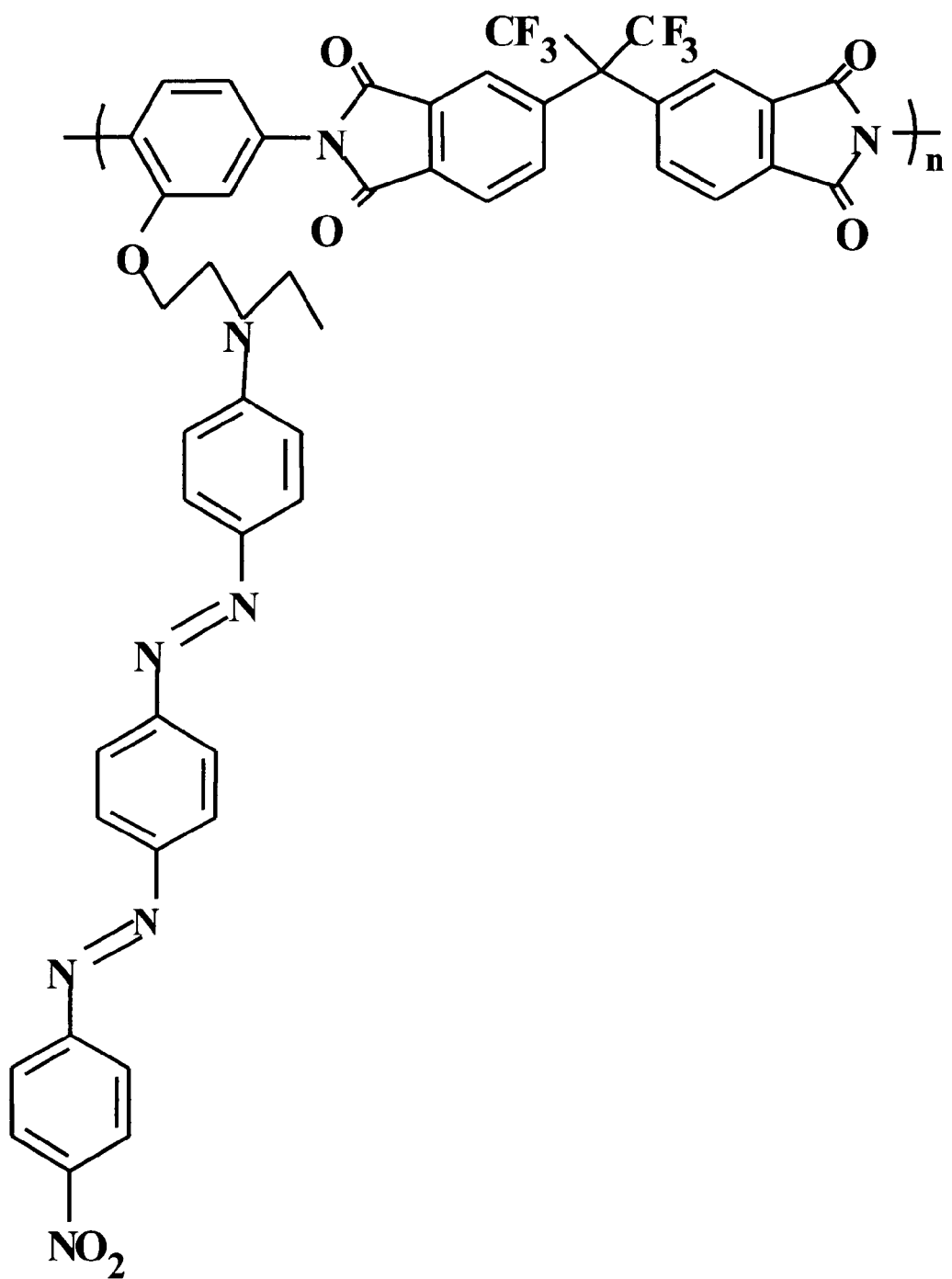
FIG. 3 depicts the chemical structure of polyimide-dialkyl amino nitro diazo. Symbol: n, ranging from about 44 to about 600.
Figure 4:
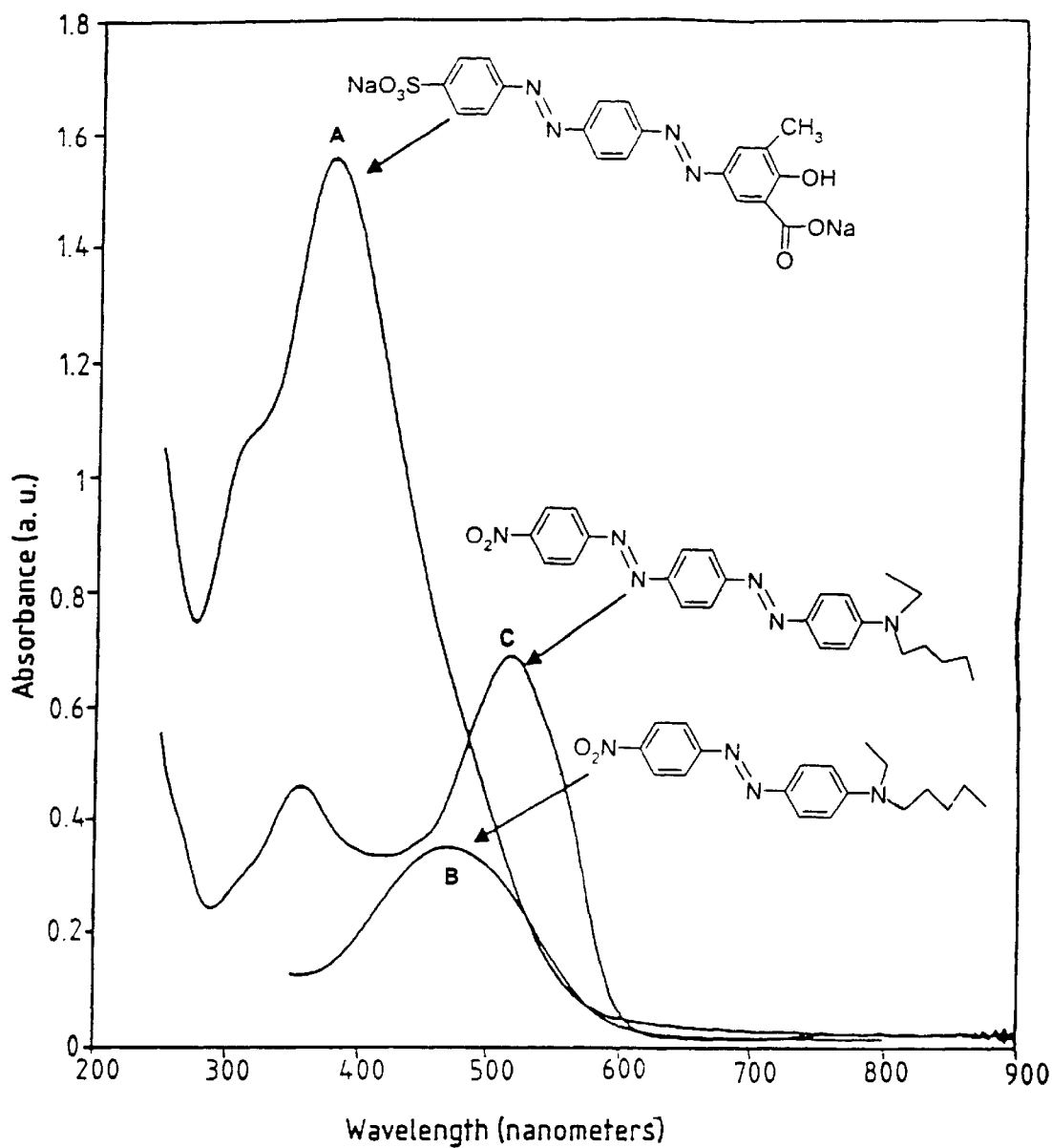
FIG. 4 shows the absorption spectra in terms of arbitrary absorbance units (0 to 1.8) at an applied wavelength (250 to 800 nm) of three second-order nonlinear optical polyimides having different pendant chromophores—i.e., sulfone diazo (Mordant Orange 10) (e.g., present in a polyimide-alkoxy sulfone diazo or poly(methyl methacrylate ) host matrix) ("A" peak), dialkyl amino nitro azo present in polyimide-dialkyl amino nitro azo ("B" peak), and dialkyl amino nitro diazo present in polyimide-dialkyl amino nitro diazo ("C" peak). For this figure, three different absorbances are superimposed. The absorbances are obtained from different thickness films and do not correspond to scale.

The chemical structures of certain of the preferred polyimides to be used for the proposed device according to the invention are shown in FIGS. 1–3, with the corresponding absorption spectra of the corresponding polymers being shown in FIG. 4. These materials provide great flexibility in terms of chemical modification, such modification which may be desirable in optimizing the properties of the polymer for use in optical applications. For instance, in dialkyl amino nitro diazo it is possible to change the electron donor in the chromophore from nitrogen to oxygen and the electron acceptor from nitro to sulfone to get the alkoxy sulfone diazo (Mordant Orange 10). This will shift the absorption maximum of the material from 532 nm to 386 nm as shown in FIG. 4.

Therefore, by changing the pendant chromophore in the polyimide employed in the different layers of the device according to the invention, different absorption peaks for the waveguide incorporated in the biosensor can be obtained. The concentration of chromophores can be carefully adjusted by copolymerization to control the refractive index at the expense of the nonlinearity (e.g., as described in Girton et al., supra, and Keil, supra).

In certain applications further described below, the structure of the polymer further is modified in that it includes a so-called analyte binding partner (ABP). Such a polymer according to the invention preferably can be depicted by Structure IV:

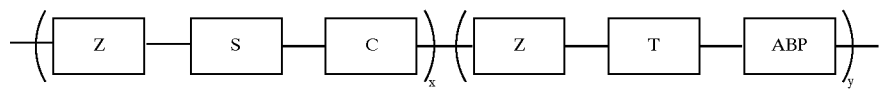

Structure IV where the numeric value of x+y (i.e., x combined with y) ranges from about 44 to about 600, and desirably ranges from about 100 to about 300. Desirably, the value of x is equal to or greater than the value of y, with x:y ratios preferably varying from about 1:1 to about 9:1. Generally, any appropriate ratio to form the polymer structure can be employed so long as: (1) the resulting polymer exhibits 2°-NLO activity; and (2) the resulting polymer is capable of binding with the analyte to form an analyte binding partner pair.

As depicted in Structure IV, "Z" is as previously defined, "T" is a so-called tether sequence, and "ABP" is the analyte binding partner. The tether sequence "T" generally, is any group that allows subsequent attachment of the analyte binding protein (ABP). However, the tether sequence exhibits the further optimal characteristics in that it can be longer than that spacer, ranging from 0 to about 300 carbon atoms, preferably from 0 to about 30, and even more desirably from 0 to about 6 carbon atoms. Also, the carbon chain can optionally be further substituted with nitrogen, oxygen, and/or sulfur. For attachment of the ABP to the tether (or directly to the polymer structure of the waveguide) basically any means of attachment that allows that advantageous properties of the invention described herein can be employed.

According to the invention, and, as further described below, a waveguide that exhibits 2°-NLO properties can be obtained not only by chemical conjugation of a 2°-NLO chromophore into a polymer backbone, but also desirably can be obtained by merely mixing a 2°-NLO chromophore with a polymer backbone in a process commonly known as "doping". For "doping" it is preferred that the concentration of the chromophore be between about 3% and about 10% of the total polymer mixture. Similarly, it is contemplated by the present invention that a polymer backbone having a 2°-NLO chromophore attached can be merely mixed (i.e., instead of present in the same polymer with) a polymer backbone having an analyte binding partner attached. Other variations such as would be obvious to one skilled in the art are contemplated by the invention.

Waveguide Sensing Device (Single Interferometer)

As indicated previously, the present invention provides a waveguide sensing device that preferably comprises:

(a) an input port;

(b) a modulator arm;

(c) a sensor arm;

(d) an output port; and (d) a detector.

Figure 6A:
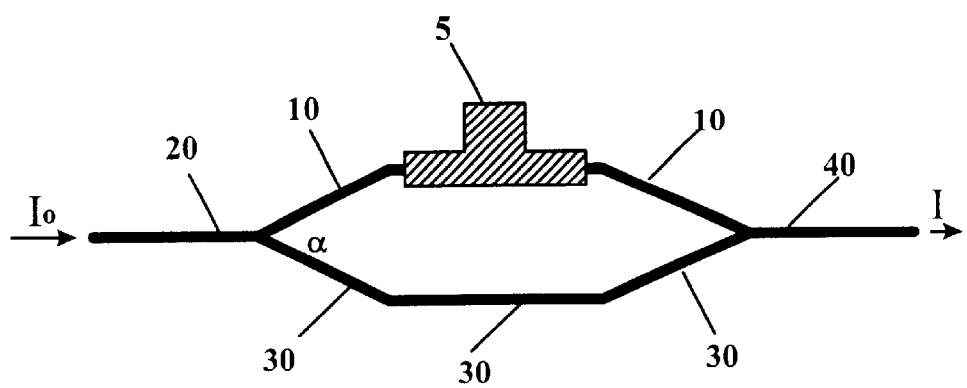
FIGS. 6A–B is a schematic diagram of a Mach-Zehnder waveguide interferometer having an input and output port, modulator arm, and sensor arm, wherein the sensor comprises a waveguide layer that is modified by attachment of the receptor/catalyst modifier by either noncovalent (i.e., Device Type A) or covalent (i.e., Device Type B) means as described herein. Symbols: 5, electrode (i.e., bottom and top electrodes); 10, modulator arm; 20, input; 30, sensor arm; 40, output; 50, 2°-NLO polymeric material; 60, solid support; *, receptor/catalyst modifier; α, branching angle.
Figure 6B:
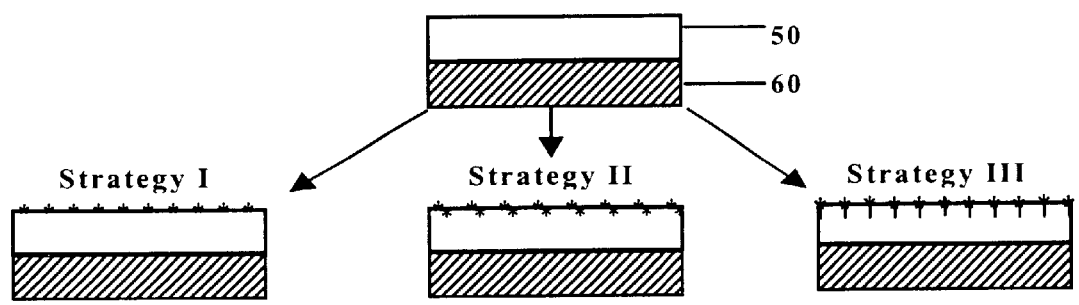
Figure 7:
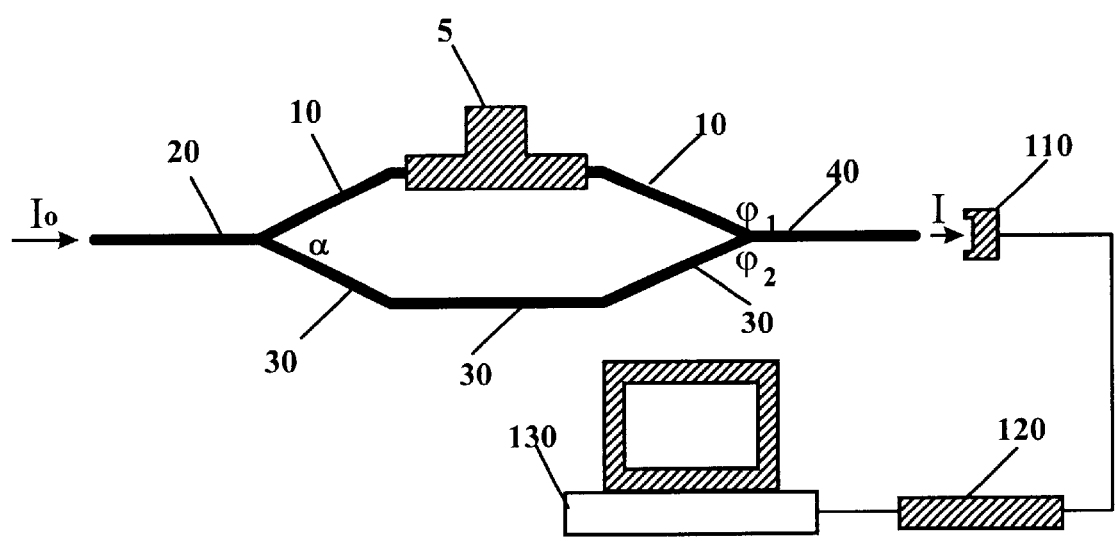
FIG. 7 is a schematic diagram of optical and electrical components of a receptor/catalyst-modified waveguide sensor according to the invention comprising input and output ports, a modulator arm, a sensor arm, a detector, and a computer. Symbols: 5, electrode (i.e., bottom and top electrodes); 10, modulator arm; 20, input; 30, sensor arm; 40, output; 110, detector; 120, lock-in amp; 130, computer; α, branching angle; I, intensity of optical output of the interferometer; $I_o$, intensity of the optical input to the interferometer; $\phi_1$ and $\phi_2$, optical phases of the wavefronts at the combining point; $V_\pi$, applied voltage for a π phase shift.

This is accomplished by the present invention inter alia by the preparation of a number of "parent" Mach-Zehnder waveguide interferometers (e.g., as depicted in FIG. 6A–B and 7), although alternate arrangements are possible and are contemplated by the invention. The overview of the preferred process for constructing the new devices according to the invention is summarized in FIG. 8, composed either of a pure second-order nonlinear optical (2°-NLO) polymer (UCP) or an 2°-NLO methyl ester-modified copolymer (MMP) (FIG. 8).

Figure 8:
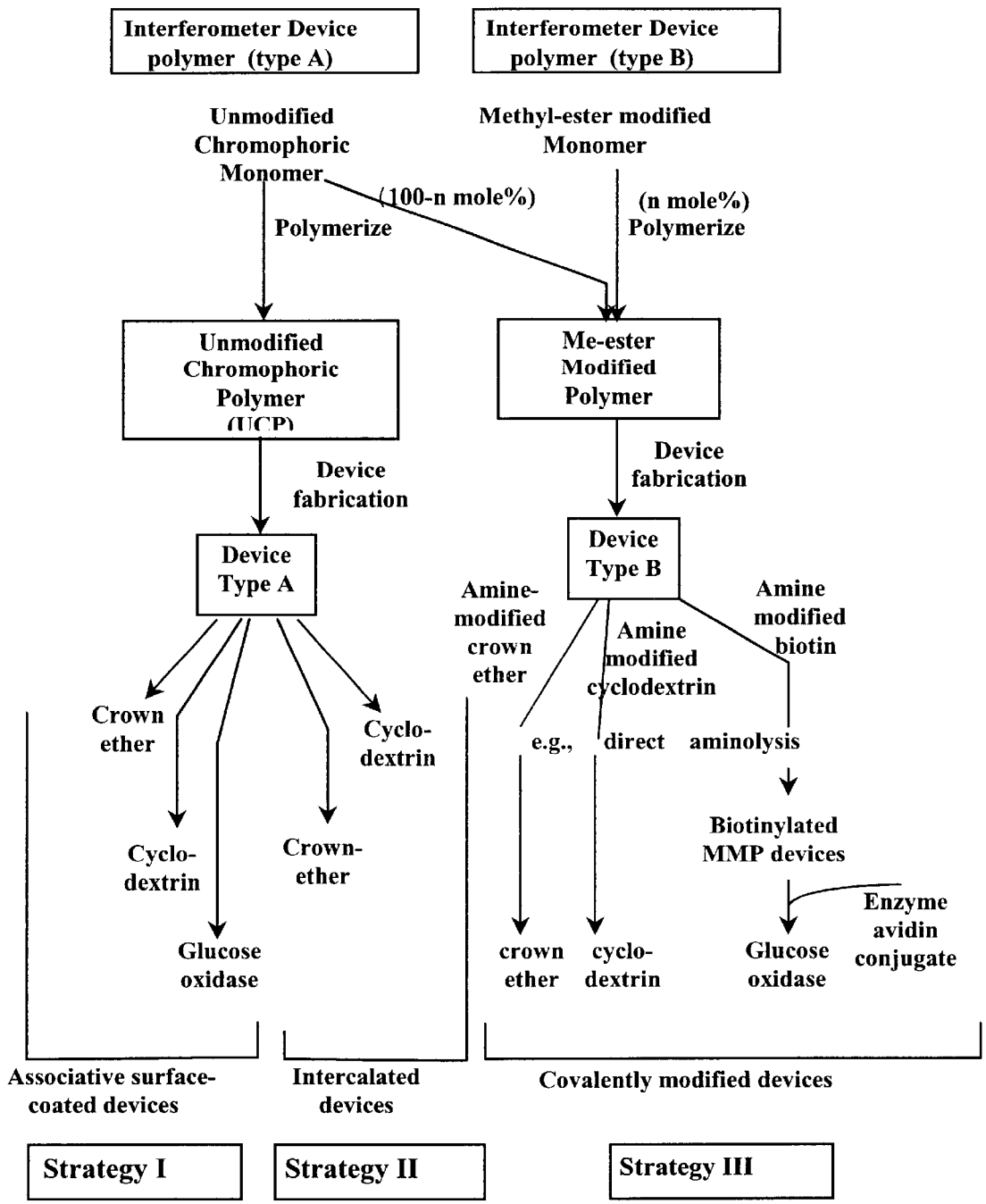
FIG. 8 is a schematic diagram of preferred control and experimental devices (Type A and B, respectively) according to the invention comprising "Associative surface-coated devices" ("Device Type A"), "Intercalated devices" ("Device Type A"), and "Covalently modified devices" ("Device Type B"). As depicted in this figure, the devices can be fabricated from unmodified chromophoric polymer ("UCP") that does not contain an analyte binding partner directly forming part of the polymer structure, or can be fabricated from methyl ester modified polymer ("Me-ester Modified Polymer"; "MMP") that is obtained by the copolymerization of an unmodified chromophoric monomer (i.e., a monomer that incorporates a 2°-NLO chromophore) and a methyl-ester modified monomer.

The first type of polymer (i.e., the unmodified polymer) is used to construct both an "experimental control" device, and identical devices differing only in the noncovalent modification of their "sensor arms" (e.g., Device Type A, FIG. 8). The second type of polymer, the copolymer, has sites for covalent modification by a "analyte binding partner", and therefore is covalently modified on its sensor arms. In each case, the modifying analyte binding partner is chosen for its interaction with an analyte of interest (as depicted in FIGS. 6A–B). The present invention accordingly provides waveguide sensing, via modification of the sensor arm of waveguides fabricated from soluble, second-order nonlinear optical (2°-NLO) polymers (FIGS. 6A–B and 7). The two preferred types of polymer-differentiated Mach-Zehnder waveguide sensors (interferometers) according to the invention will be referred to herein simply as Device Type A and Device Type B as indicated in FIG. 8, and as further dicussed below.

As depicted in this FIG. 8, the devices can be fabricated from unmodified chromophoric polymer ("UCP") that does not contain an analyte binding partner directly forming part of the polymer structure, or can be fabricated from methyl ester modified polymer ("Me-ester Modified Polymer"; "MMP") that is obtained by the copolymerization of an unmodified chromophoric monomer (i.e., a monomer that incorporates a 2°-NLO chromophore) and a methyl-ester modified monomer.

In terms of prerequisite monomers and polymers needed for preparing the Device Types A and B, the monomeric organic molecules needed for polymerization can be prepared by published methods or simple modification of same, as described in the Examples which follow. The diamine molecule (termed the "Unmodified Chromophoric Monomer", or "UCM") employed in fabrication of Device Type A (FIGS. 3, left column) and its required anhydride partner desirably can be copolymerized to form what is termed the "Unmodified Chromophoric Polymer" (i.e., "UCP"; sample UCP depicted in FIG. 9). Alternately, the UCP can be purchased, or synthesized merely by chemically modifying an already known polyimide by methods that are known to those skilled in the art (e.g., as described in D. Yu, A. Gharavi and L. Yu, "Novel Second Order-Nonlinear Optical Aromatic and Aliphatic Polyimides Exhibiting High Temperature Stability", *Appl. Phys. Lett.* 60, (1995) 1050–1052). Generally, the UCP is simply a polyimide backbone as previously described that has been combined (optionally by means of a spacer) with a 2°-NLO chromophore. Various UCPs according to the invention have been characterized for their optical properties, and are adequate for the purposes of the proposed device as set forth in Table 2.

TABLE 2

Summary of relevant physical parameters for ether- and amine- linked, chromophore-containing polymers.

| Tether-Chromophore Linkage | Electrooptic coefficient ($r_{33}$) | $\lambda_{max}$ | Refractive Index |
|---|---|---|---|
| ether | 4.5 pm/V | 340 nm | ≈1.6 |
| amine* | 6.1 pm/V | 390 nm | 1.7 |

*Described in D. Yu, A. Gharavi and L. Yu, "Novel Second Order-Nonlinear Optical Aromatic and Aliphatic Polyimides Exhibiting High Temperature Stability", Appl. Phys. Lett. 60, (1995) 1050–1052.

Figure 9:
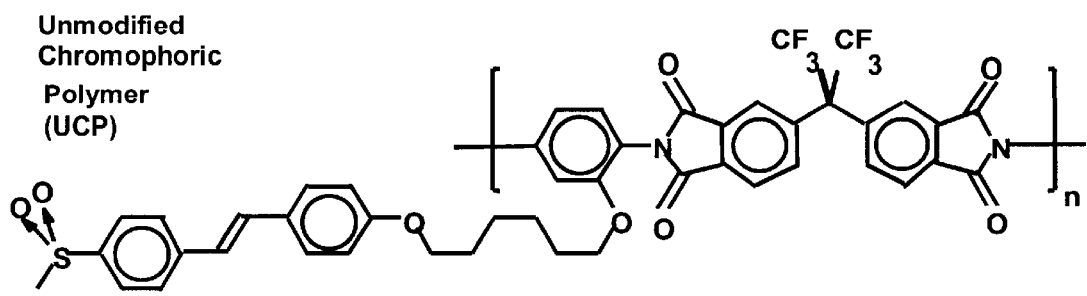
FIG. 9 depicts the synthesis of a sample unmodified chromophoric polymer (UCP) according to the invention, polyimide-alkoxy sulfone stilbene. Symbol: n, ranging from about 44 to about 600.

The difference in the polymers recited in Table 2 lies in the atom by which the chromophore is tethered to the polymer. The case of the ether tether is depicted in FIG. 9, where it can be see that the oxygen atom is para to the stilbene double bond. This atom is replaced by an ethylated nitrogen (Table 1, chromophore 1) in the second of the available NLO polymers, Table 2.

A modified polymer is needed for Device Type B (FIG. 8, "methyl-ester modified monomer"), and toward this end, the present invention provides a simple route to synthesize the necessary variant monomer needed for construction of the polymer, wherein the chromophore preferably is replaced by a six carbon chain with a carboxylic acid terminus, or by other appropriate modification. The terminus is chemically "protected" through subsequent polymerization and fabrication, but is "deprotected" thereafter. After copolymerization of this variant diamine and the chromophoric diamine (with the former as a small fraction of the latter), the product Methyl-ester Modified Polymer (MMP, FIG. 10B)—is purified and used to fabricate Device Type B. The MMP should have physical and electrooptic properties appropriate for use in the invention (Yu et al., *J Amer. Chem. Soc.* 117 (1995) 7295; Yu et al., "Highly Stable Copolymides for Second Order Nonlinear Optics" *Macromolecules* 29 (1996) 6139–6142. Further details of this synthetic reaction are set out in Example 1.

In terms of fabricating the devices of the invention, the procedure preferably is performed repeatedly, providing waveguides composed of either UCP (Device Type A) and MMP (Devices Type B). The device substrate preferably is prepared by layering poly(methyl methacrylate) (PMMA)—a second, different polymeric layer with refractive index less than that of the two synthetic polymers in use—onto an aluminum-coated glass square, by the well known process of "spin-coating". The PMMA thus serves as "cladding". The synthesized polymers are then spin-coated onto the clad aluminum surface to a thickness of about 1 $\mu$m.

This supported polymer then preferably is overlain with a commercially produced, chromium-coated glass "mask" in the familiar, extended hexagonal shape of the Mach-Zehnder waveguide (i.e., as depicted in FIGS. 6A–B and 7). The masked, supported polymer is then exposed to ultraviolet light, "bleaching" the unmasked areas and destroying exposed chromophore therein. After unmasking the supported material—now a waveguide—the chromophoric side chains of the polymer are aligned ("poled") by heating the waveguide to a temperature greater than the characteristic temperature at which the polymer strands, branchings, etc., have sufficient thermal energy to allow reorientation (i.e., the "glass transition temperature", $t_g$; ≈240° C. for UCP). Concomitantly, a high-voltage potential is created across the waveguide (negative at the aluminum face, positive at the polymer face; standard "corona poling"). As a result, the axes of the dipoles of the chromophores after poling are, on average, oriented perpendicular to the plane containing the waveguide, and the "end" of the chromophore that has the more electron-withdrawing substituent is directed toward its unclad face.

A layer of PMMA cladding then desirably is added to the unclad face of the poled waveguide (again, e.g., by spin coating). The freshly clad face of the poled waveguide is then masked (by a piece of thin aluminum plate engraved with the shape of an electrode plate), leaving one of the two arms of the interferometer—"the modulator arm"—exposed (FIGS. 6A–B and 7). A layer of gold (less than about 0.1 $\mu$m) is then deposited on the unmasked area on the modulator arm of the unit (by "vacuum evaporation"), creating the attachment site of an electrode on this arm. The unit is then unmasked. Finally, careful removal of the area of the recently added cladding on the surface of the waveguide immediately above the other arm of the interferometer— "the sensor arm"—exposes the underlying 2°-NLO polymer, and completes the fabrication stage.

The sensor arm also desirably can be modified. Namely, the two preferred waveguides according to the invention are those composed of UCP (i.e., "Device Type A") and those composed of MMP (i.e., "Device Type B"). These devices are obtained by treatment with appropriate modifying agents as defined by three strategies (i.e., depicted in FIGS. 6A–B, and further described in FIG. 8) and which are as follows. Namely, for application to both Device Type A as well as Device Type B, the present invention provides for:

(1) "Associative Surface Coating", or the association of an analyte binding partner (e.g., such as a "receptor" or "catalyst" molecule) with the surface of the polymer without chemical bond formation (i.e., noncovalent association); and (2) "Intercalation", or the association of an analyte binding partner (e.g., such as a "receptor" or "catalyst" molecule) with sites present both on the surface and within the polymer film (i.e., via "swelling" of the pre-formed polymer matrix), again, by noncovalent association.

The present invention further desirably provides for application only to Device Type B, "Covalent Surface Modification", or the derivatization of the protected termini of sites of the MMP chains (i.e., the small percent of the total strands which have the chromophore replaced by the six carbon chain with the protected terminus), resulting in formation of a covalent (i.e., strong) bond between the termini and various analyte binding partners (e.g., such as a "receptor" or "catalyst" molecules).

Details of the modification procedures are well documented in the scientific literature, but nevertheless are discussed further below. In general terms, the modifications preferably involve either surface application of the receptor/catalyst in a carrier solvent to the area of the 2°-NLO polymer (i.e., UCP/MMP) on the sensor arm of the waveguide from which the cladding has been removed, followed by a period of equilibration and evaporative removal of the carrier solvent (i.e., associative surface coating strategy, and covalent surface modification). Alternatively, the modification desirably involves prior treatment of the same unclad polymer surface (i.e., in a separate device) with solvents and other agents that result in slight "swelling" of the 2°-NLO polymer layer. Subsequent application of the receptor/catalyst then has the potential to diffuse to the volume within the 2°-NLO polymer, rather than merely remaining at its surface (i.e., intercalation strategy).

Figure 11A:
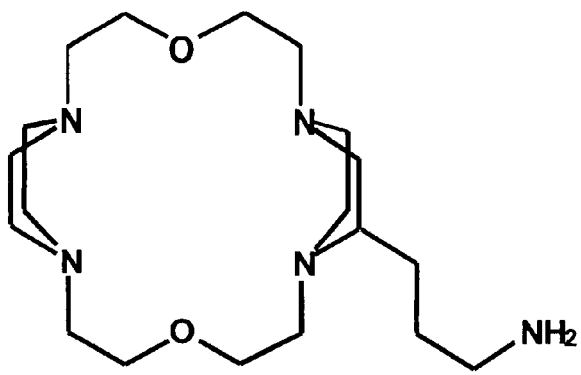
FIGS. 11A–C depicts the sources of three amine-functionalized modifying agents employed in the invention: cryptand-modified polymer (A), β-cyclodextrin-modified polymer (B), and glucose-oxidase-(avidin-biotin)-modified polymer (C).
Figure 11B:
Figure 11C:
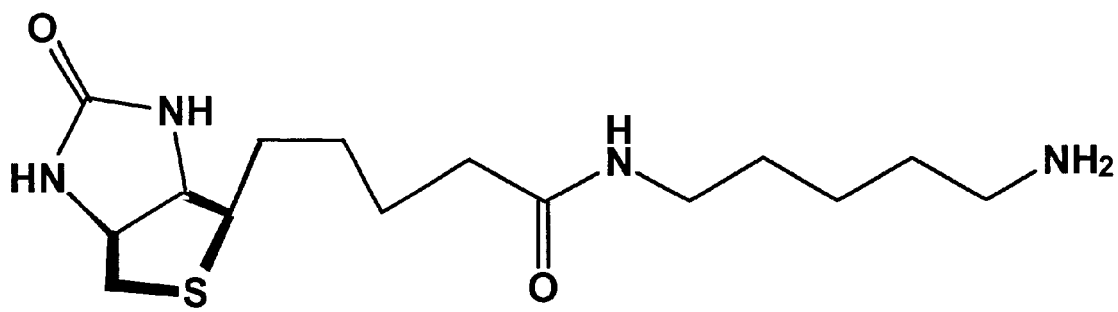

The receptor/catalyst types that will be used—seen as identifying labels on the arrows leading from Device Type A and from Device Type B (in FIG. 8)—are prepared as shown in FIG. 11A–C. In associative surface coating, intercalation, and covalent surface modification strategies, the receptor/catalyst types that will be employed desirably are: (a) very specific ion-selective macrocycles (i.e., including, but not limited to a modified, lead(II) cation-specific "Hancock cryptand" (FIGS. 11A); and (b) broadly selective cyclo-oligosaccharides—binding organics (e.g., phenols, carboxylates, etc.) and drugs (tryptamines, hydantoins, barbitals, etc.), including but not limited to the (+)-mephobarbital-selective β-D-cyclodextrin (FIG. 11B). For use only with associative surface coating and covalent surface modification strategies, the receptor/catalyst types that will be employed desirably are metabolite-selective receptors/enzymes, including but not limited to the popular redox-active, glucose-specific enzyme, glucose oxidase, here attached as a conjugate to the milk protein avidin, which binds to the low M.W. ligand biotin (FIG. 11C). In the case of associative surface coating and intercalation, the commercial or otherwise readily available "parent" receptors preferably are used (i.e., the unmodified Hancock-cryptand, unmodified β-cyclodextran, and ordinary biotin).

The three receptor/catalyst polymer modifiers shown boxed in FIGS. 11A–C, and the related, parent compounds preferably are used as follows. First, the parent molecules desirably are used directly to modify the sensor arms of Type A and Type B Devices by associative surface coating and intercalation as described above. Second, for covalent surface modification, the synthetically prepared reagents shown in FIG. 11 desirably are used to covalently modify the MMP-containing sensor arm of Type B Devices. In its simplest fashion, this covalent modification desirably will take the form of a direct aminolysis reaction by the reagents of FIG. 11A and FIG. 11B, whereby the "protecting group" on the special side chain of the MMP strands (MMP, FIG. 10B) is directly displaced by the amine group of the incoming receptor/catalyst modifier. Of course, the conditions of this modification reaction are optimized empirically (Bodanszky et al., *The Practice of Peptide Synthesis*, (Berlin: Springer-Verlag, 1994); March, *Advanced Organic Chemistry: Reactions, Mechanisms, and Structure* (NY: John Wiley & Sons, 1992); Kocienski, *Protecting Groups* (NY: Georg Thieme Verlag, 1994); Kvita, "Synthese von 2(1H)-Pyridonen aus 2H-Pyran-2-onen", *Synthesis* (1991) 883–884)). The cryptand and cyclodextran-modified polymers are shown in schematic form in FIG. 12 (left and center) with bound analytes indicated.

The "covalent" modification by glucose oxidase using covalent surface modification is slightly more complicated, but is nevertheless straightforward. Desirably, modification is accomplished by a covalent step and by a subsequent noncovalent step. The noncovalent step is so high in energy-of-association that for all intents and purposes, it can be considered as well to be irreversibly bound. In this case, desirably the aminolysis reaction is performed with reagent 11C (FIG. 11C), such that the result is an MMP-containing sensor arm (Type B Device) with biotin attached to the 2°-NLO polymer. When such covalently modified devices are further treated with a solution of avidin—a commercially available milk protein—the well-documented (aforementioned high energy) association between avidin and biotin will take place. Here, however, the avidin used will be avidin per se as well as another commercially available molecule to which glucose oxidase has been attached so that the avidin-biotin interaction between the biotinylated device and the avidin-glucose oxidase conjugate results in a glucose oxidase-modified device. The latter polymer, so modified, is illustrated in schematic for bound glucose in FIG. 12C.

Use of the Sensing Devices in Detecting Analytes

Desirably, the finished waveguide sensing device with the modified sensor arm (shown in schematic in FIG. 7) is connected to a controlled, low-voltage DC source via its modulator arm (10). Its input port (20) preferably is connected to a light source such as a laser (e.g., diode, He—Ne, etc.) via a fiber optic or by direct end coupling, or similar device. The output port (40) of the device is similarly preferably is connected via its output port to a commercially available detector-amplifier assembly (110, 120). The amplified signal is then desirably coverted to a digital signal and monitored in real-time by a standard microcomputer (130), such as a 120 Mhz IBM PC.

Experimental testing and use of the finished devices desirably involves establishing a null (baseline or benchmark signal) for the receptor/catalyst-modified Device which as of the time of testing for the baseline or benchmark signal, is untreated by analyte. Desirably, this signal can be adjusted via the voltage to the modulator arm. In terms of sensing, first the null condition (i.e., condition where no analyte is present) is assessed empirically. Then, preferably the sensor is put in contact with analyte. This changes the output signal, and the rate of change of the signal is then observed in response to the addition of the analyte to the surface of the receptor/catalyst-modified 2°-NLO polymer in the sensor arm of the device, relative to the solution lacking the analyte. The magnitude of change (sensitivity) depends on how many analytes (e.g., antibodies) have attached.

Thus, the present invention provides a method of detecting an analyte, the method preferably comprising:
  (a) obtaining a waveguide sensing device according to invention;
  (b) contacting the waveguide with a sample that does not contain analyte and assessing the signal from the output port;
  (c) contacting the waveguide with a sample to be tested for the presence of analyte and assessing the signal from the output port; and
  (d) comparing the signal assessed from the output port upon contacting with a sample to be tested for the presence of analyte relative to contacting with a sample that does not contain analyte, and any difference being due to the presence of the analyte.

Desirably according to this method, the amount of the analyte is determined by the rate of change of the signal assessed from the output port with addition of the sample as compared to with no addition of the sample.

The range of analyte concentrations to employ in the testing according to the invention desirably is based on standard, published protocols for each analyte-receptor/catalyst combination. In particular, various concentrations of solutions of lead salt (relevant toxicity range, 10–100 $\mu$g/dL, *Merck Manual*, 16$^{th}$ Edn., P. 2125) and other metal ions (nickle, zinc, cadmium, etc.) preferably are examined using Hancock cryptand-modified Devices ($K_{dis} \cong 10^9$ for $Pb^{2+}$, versus unmeasurable for other metals). Other tests of the sensor desirably include the ability to detect the barbiturate (+)-methyl barbital and discriminate it from its enantiomer, with the β-cyclodextrin-modified Devices, and the ability to sense the association of two proteins (i.e., unconjugated avidin and glucose oxidase-conjugated avidin) with the biotinylated Device ($K_{dis} \cong 10^{15}$). Still further tests of the sensor preferably include the ability to sense the presence of commercially available molecules (e.g., enzyme substrate (βD-glucose, either alone and in the presence of product (D-glucononic acid δ-lactone) and inhibitor (D-glucal)) by the glucose oxidase-modified Device (i.e., after association of glucose oxidase-conjugated avidin with the biotinylated Device).

Figure 12A:
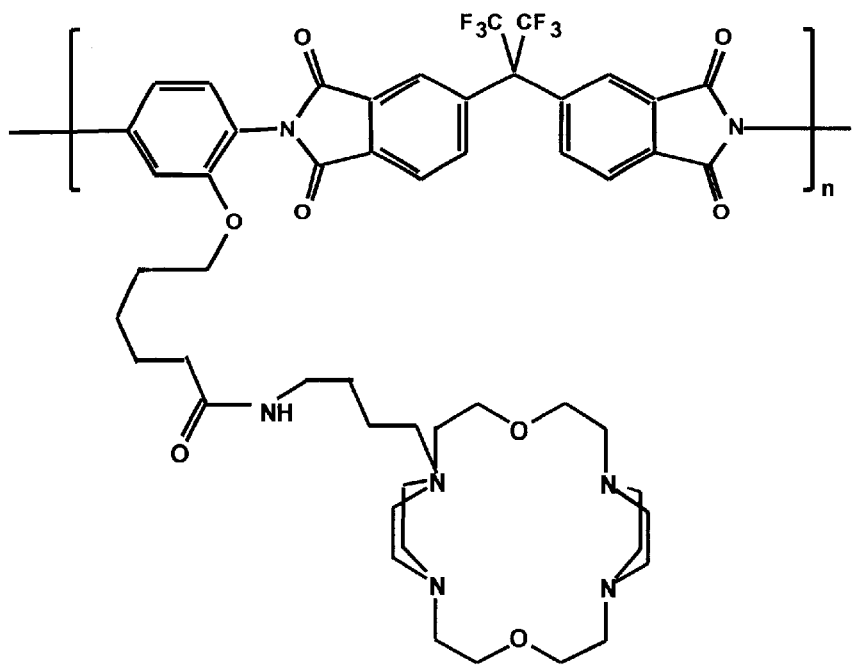
Figure 12B:
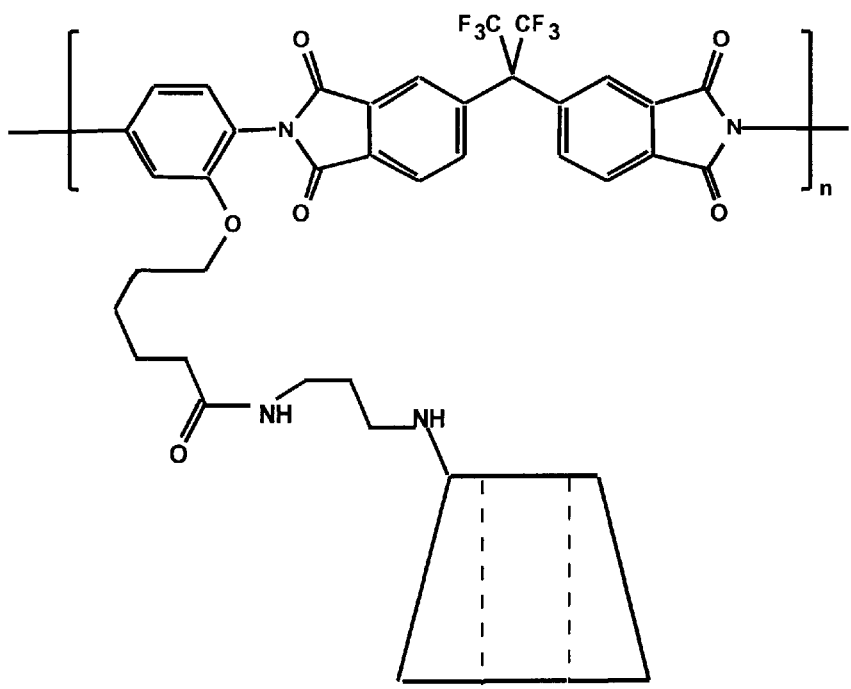

The modified polymers corresponding to the cryptand-modified device, the β-cyclodextrin-modified device, and the glucose-oxidase-modified device are shown in schematic form in FIG. 12A–C. For the variety of these tests, the successful demonstration of the effect would be manifest in an observed increase in signal, not discounted by controls. These combinations should yield at least one combination of analyte and receptor/catalyst which will be amenable to broad sample solvent and solute background studies.

Analytical methods to detect the presence of chemical and biological agents and their byproducts are necessary fundamentals en route to understanding the acute and chronic effects of exposure to such agents on human health, on the environment, etc. Ideally, such technologies should, in addition to being sensitive and accurate, have one or more of the following characteristics: (1) capabilities for remote, continuous, long-term monitoring; (2) adaptability to real-time, in situ monitoring applications; (3) compact construction with possibility of miniaturization; (4) robust construction; (5) ease of fabrication; and (6) low cost of production. The present inventive family of biosensors appear to satisfy these criteria.

Waveguide Sensing Device (Double Inteferometer)

Each device according to the invention desirably is tested for sensitivity to its analyte under various conditions, and relative to controls. The invention further desirably provides a double interferometer as depicted in FIGS. 15A–B (top views) and 16 (side view) that optimally can be employed for sensing should it be necessary to compensate for non-specific effects.

Figure 16:
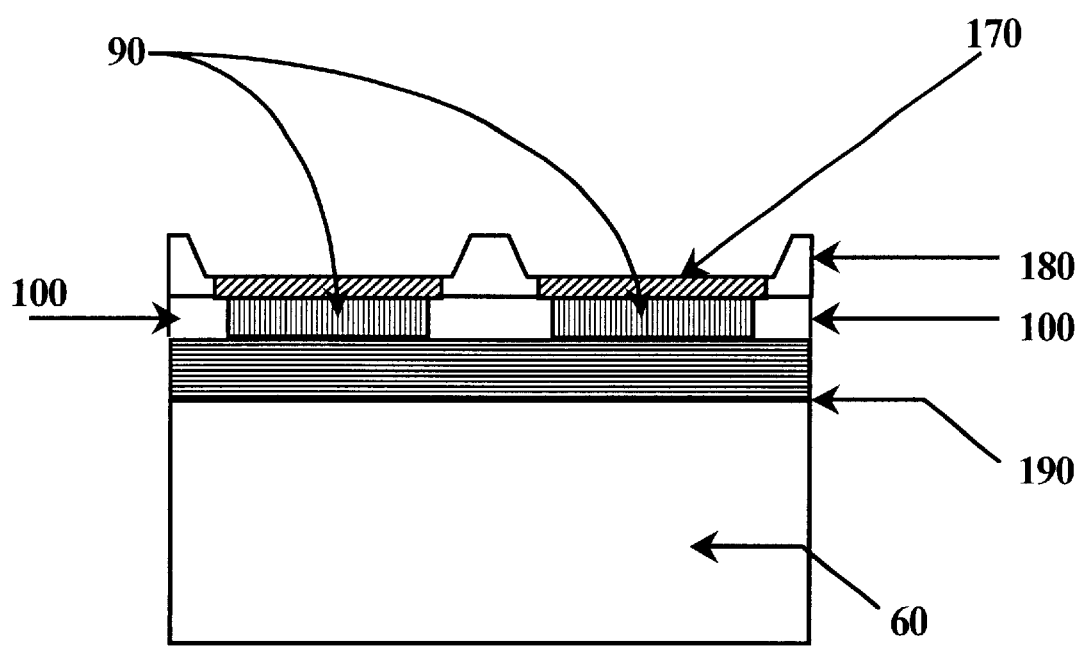
FIG. 16 is a schematic representation (as seen from the side) of a double Mach-Zehnder interferometer including waveguide and electrode layouts. Symbols: 90, waveguide.

In terms of the structure of this double interferometer, the sensing device desirably has the structure depicted in FIG. 16, although alternate arrangements are possible and are contemplated by the invention. As depicted in FIGS. 15A–B, preferably two interferometers are fabricated side-by-side on the same solid support (e.g., glass substrate). The interferometers are arranged such that the separate sensor arms (30) of each of the inteferometers are next to each other on the support and desirably comprise a region (called the "Sensor Area" (165), FIG. 15B) to which analyte can be applied. Preferably, only the sensor arm of one of the interferometers is modified by the analyte binding partner (e.g., by the receptor/catalyst of choice) so as to comprise the "bio-activated arm" (150). Optimally, the other sensor arm is not so modified by analyte binding partner and functions as the "reference arm" (160).

Of course, what is not shown in FIGS. 15A–B is the fact that, optimally, both output ports (i.e., both I and $I_r$) are each connected to their own respective detectors, which in turn, are each connected to their own respective lock-in amp, if necessary. Each of these lock-in amps then desirably communicates with a computer, which assesses the information. It further is conceivable that both output ports (i.e., both I and $I_r$) are each connected to the same detector, but this would require some manipulation of the set up. Of course, this is all within the skill of the ordinary investigator.

Thus, the present invention provides a waveguide sensing device that preferably comprises:

(a) a first and second input port (i.e., a reference and signal input port);

(b) a first and second modulator arm;

(c) a first and second sensor arm, only one of which has been modified with an analyte binding partner so as to comprise the bioactivated arm, the other comprising a reference arm;

(d) a first and second output port (i.e., a reference and signal output port), the first output port connected to the first modulator arm and the first sensor arm, and the second output port connected to the second modulator arm and the second sensor arm; and (e) a detector, the waveguide being comprised of an optical nonlinear second-order polymer.

This double interferometer desirably can be employed in a method of detecting an analyte, the method preferably comprising:

(a) obtaining such a double interferometer that can be employed as a waveguide sensing device;

(b) contacting the first and second sensor arm with a sample to be tested for the presence of analyte;

(c) assessing the signal from the first and second output port; and (d) comparing the signal assessed from the first output port relative to the signal assessed from the second output port, with any difference being due to the presence of the analyte.

The method optimally provides that the binding of the analyte is determined by the comparative rate of change of the signal assessed from the output port. Use of such a device optimally further provides for subtraction of any solvent effect, as set out in the following Examples.

The following examples further illustrate the present invention but, of course, should not be construed as in any way limiting its scope.

EXAMPLE 1

Chemical Technologies and Synthesis

This Example describes an exemplary chemical synthesis of the monomer, polymer, and other modifications of the material according to the invention.

Figure 10A:
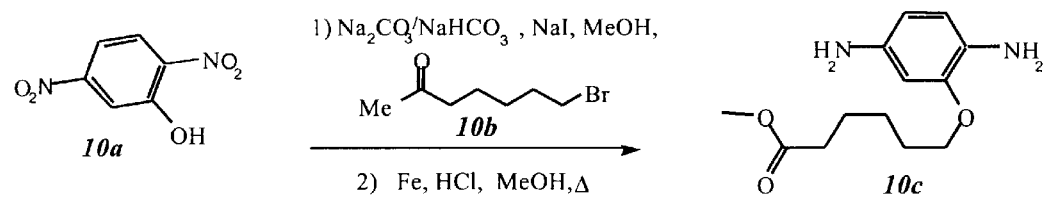
FIGS. 10A–B depict the synthesis of the methyl ester-modified polymer (MMP) according to the invention. Symbol: n, ranging from about 44 to about 600. Structures: 10a, dinitro phenol; 10b, bromo ester; 10c, para-diamino-phenol; 10d, dianhydride.

Reagents necessary to carry out synthesis are commercially available. The preparation of the necessary monomer, polymer, and modification materials are depicted in FIG. 9 (synthesis of unmodified chromophoric polymer (UCP), FIG. 10 (synthesis of the methyl ester-modified polymer (MMP)), and FIGS. 11A–C(synthesis of three amine-functionalized modifying agent), and is described, among others, in the references of Chae et al., "New Reagents for the Synthesis of Fluorescent Chemosensors, Anthrylogous Ethylene Dibromides", *J. Org. Chem* 58 (1993) 5797–5801, and Tabushi et al., "Cyclodextrin Flexibly Capped with Metal Ion", *J. Amer. Chem. Soc.* 99 (1977) 7100–7103).

Namely, the polyimide-alkoxy sulfone stilbene depicted in FIG. 9, or other unmodified chromophoric polymer (UCP) according to the invention, can be synthesized as described in D. Yu, A. Gharavi and L. Yu, "Novel Second Order-Nonlinear Optical Aromatic and Aliphatic Polyimides Exhibiting High Temperature Stability", *Appl. Phys. Lett.* 60, (1995) 1050–1052.

Figure 10B:
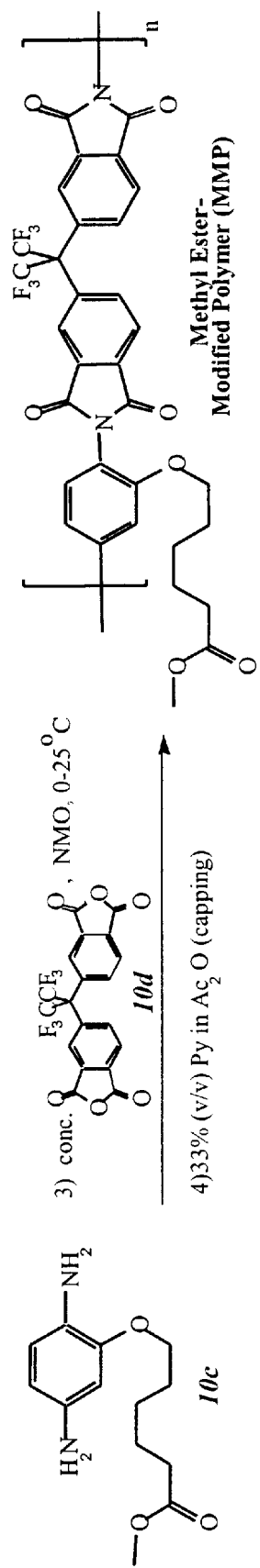

Similarly, the MMP depicted in FIG. 10B can be synthesized as follows. Namely, the polyimide polymer backbone is prepared using known technology. A para-diamino-phenol (Structure "10c" in FIGS. 10A–B) is prepared having an appropriately terminated alkyl group (in this case an ester terminus, Structure "10c" in FIGS. 10A–B). The resulting diamino phenol is then used from the outset of the synthesis if the amine groups are suitably protected (e.g., usually as phthalimides). The side chain then is attached to the tether by simple phenolic alkylation using the requisite bromo ester (Structure "10b" in FIG. 10A). Alternatively, the amine functionalities in the polymer backbone are obtained from nitro groups of dinitro phenol (Structure "10a" in FIG. 10A) that can be reduced chemically ($SnCl_2$/HCl, Fe/HCl) to yield the desired diamino phenol. This method also has the added feature of the enhanced acidity of the nitro-phenol aiding the alkylation. The diamine (Structure "10c" in FIGS. 10A–B) and dianhydride (Structure "10d" in FIG. 10B) are condensed in two stages to give the desired polyimide. First, the two components are stirred together to give the ring-opened anhydride, the polyamic acid, in which a simple amide-acid polymer is formed. Second this polyamic acid is dehydrated to the polyimide by addition of a 2:1 (v/v) mixture of acetic anhydride and pyridine followed by heating. At the end of this reaction the methyl ester modified polyimide (MMP) is obtained.

Also, the amine-modified form of the Hancock cryptand is available in three steps by a modification of the procedure of Chae et al. (Yu et al., supra). The parent Hancock cryptand is available in a single step treatment of macrocycle (FIG. 11A) with 1,2-dibromoethylene in ethanol (Chae et al., supra). β-D-cyclodextrin modified by a 1,3-diaminobutyl linker in the 6-position is available in two steps from the known 6-O-tosylate (FIG. 11B), according to the direct precedent of Tabushi and coworkers (Tabushi et al., supra). The avidin conjugate (FIG. 11C) can be purchased from a variety of vendors (e.g., Pierce Chemical, Sigma/Aldrich, etc.).

EXAMPLE 2

Physical Properties and Principle of Operation

This Example describes the physical properties and theoretical underpinnings of the invention.

The principles described herein apply to optical fibers and waveguides in general. According to the invention, the light traveling in an optical waveguide is confined within a core surrounded by or sandwiched between layers of material with lower refractive index called cladding. This guided light in the waveguide experiences total internal reflection, if the angle of the internal incident light is smaller than the critical angle. If this angle is larger than the "critical angle" some light will escape from the waveguide. The critical internal angle $_c$ at each surface is defined by the following equation $$\Theta_c \geq \sin^{-1}(n_2/n_1)$$

where $n_1$ is the index of refraction of the waveguide core, and $n_2$ is the index of refraction of the top layer (Pease et al., "Adaptation of a Fiber-Optic Biosensor for Use in Environmental Monitoring", In *Biosensor and Chemical Sensor Technology*, K. R. Rogers, A. Mulchandani, and W. Zhou, eds., ACS symposium Series 613, (Washington, D.C.: American Chemical Society, 1995) 34). Simultaneously, the electromagnetic field at reflection points of the light extends into the surrounding media of the waveguide and its intensity decays exponentially as the distance from the surface of the waveguide increases. This is depicted in FIG. 14, which represents an evanescent wave in a waveguide of the invention, where $n_1$, $n_2$, and $n_3$ are the refactive indices of each layer, θ is the incident internal angle, 2a is the polymer waveguide thickness, and z is the penetration depth. The penetration distance, z, is less than a wavelength and depends on the incident internal angle, θ, which is in turn related to $n_1$ and $n_2$. The incident internal angle is larger than the critical angle.

The penetration depth of the evanescent wave ($d_p$) and the electric field distribution (E) for layers 1 and 2 (i.e., $n_1$ and $n_2$) are given by the following equations $$d_p = \frac{-\lambda}{2\pi n_1 \sqrt{\{\sin^2\theta - (n_2/n_1)^2\}}} \text{ and}$$

$$E = E_0 \exp\left(\frac{-z}{d_p}\right)$$

where $E_0$ is the initial electric field, and which describe the penetration that causes a change in the phase of the light (known as "Goos-Haenchen shift"), and gives rise to a phase shift between the incident and the reflected wave (Hall, *Biosensors*, (Englewood Cliffs, N.J., Prentice-Hall, 1991) 163–174); Yeh, *Optical Waves in Layered Media*, (NY: John Wiley and Sons, 1988) 72–77; Midwinter, *Optical Fibers for Transmission*, (NY: John Wiley and Sons, 1979) 33–39).

The magnitude of the Goos-Haenchen phase shift is given by the following equations $$\Phi_{TE} = 2\tan^{-1}(\sin^2\theta - n_2^2/n_1^2)^{1/2}/\cos\theta$$

$$\Phi_{TM} = 2\tan^{-1}(\sin^2\theta - n_2^2/n_1^2)^{1/2}/(n_2^2/n_1^2)\cos\theta$$

where TE refers to the transverse electric polarization of the light for a TE wave, and TM refers to the transverse magnetic polarization of the light for a TM wave (Katzir, supra; McCurley et al. supra).

As described in the above equations, changing the refractive index of the cladding, $n_2$, will result in a phase change in the evanescent light. This change can be easily detected in a Mach-Zehnder interferometer as an amplitude change. For a given change in the cladding index, Δn, the phase change for the TM wave, $\Delta\Phi_{TM}$, should be larger than the phase change in the TM wave, $\Delta\Phi_{TE}$.

EXAMPLE 3

Interferometer Background and Design

This Example describes some background on interferometers, as well as exemplary interferometer design according to the invention.

The Mach-Zehnder interferometer (e.g., depicted in FIGS. 6A–B and 7) is a common design which is widely used for intensity modulation of laser light, and takes advantage of the Pockles effect. Namely, the laser light in the waveguide reaches a fork (a "Y" branch) and is split between two parallel waveguides (arms). After a distance of being separated (i.e., defined by a variable known as "L"), the two arms are rejoined and the light traveling in the two arms recombines, resulting in constructive or destructive interference, depending on the relative phase of the combining waves. The phase of the light in each arm can be effected in several ways. The output intensity, I, of the interferometer is given by the equations $$I = \frac{I_0}{2}(1 + \cos\phi)$$

and $$\phi = \phi_1 - \phi_2$$

where $I_o$ is the intensity of the optical input to the interferometer and $\phi_1$ and $\phi_2$ are the optical phases of the wavefronts at the combining point (Girton et al., "Electrooptic Polymer Mach-Zehnder Modulator", In ACS Symposium Series 601, *Polymers for Second Order Nonlinear Optics*, (Washington, D.C: American Chemical Society, 1995) 456–468).

Since the waveguide according to the invention is composed of an active 2°-NLO material, the phase change in the modulator arm can be controlled by application of a voltage to the modulator electrodes. If $\phi_1-\phi_2$ differs by multiples of $\pi$ (i.e., by multiples of 180°), the output intensity, I, will display either a maximum or a minimum. The applied voltage for a $\pi$ phase shift is defined as $V_\pi$ and is related to the electrooptic coefficient of the NLO polymer, $r_{33}$, of which the waveguide is composed, by the following formula:

$$V_\pi = \lambda h / n^3 r_{33} L$$

where h is the electrode spacing, $\lambda$ is the wavelength of incident light, n is the refractive index of the waveguide ($n_1$), and L is the length of the waveguide arm under the electrode.

EXAMPLE 4

Waveguide Design

This Example describes exemplary waveguide design according to the invention.

For a Y-branch Mach-Zehnder interferometer, two of the most important quantities are the branching angle ($\alpha$) and the width (w) of the waveguide (shown in FIGS. 6A–B) (Ranganath et al., "Ti Diffused LiNbO$_3$ Branched-Waveguide Modulators: Performance and Design", *IEEE Journal of Quantum Electronics*, QE-13 (1977) 290–295). The angle $\alpha$ is chosen so that the total internal reflection criteria are met. For example, a bleached homopolymer with refractive indices of the $n_1$ and $n_2$ layers of about 1.7 and 1.65, respectively will give a critical angle of 76.06° to provide total internal reflection, suggesting that the half-angle of the fork should be smaller than 12.94°.

The width of the waveguide is determined empirically, such that the waveguide supports a single mode of propagation and still has a large cross-section (see, Soref et al., "Large Single Mode Rib Waveguides in GeSi—Si and Si on SiO$_2$", *IEEE Journal of Quantum Electronics*, 27 (1991) 1971–1974; Fishbeck, R. Moosburger, M. Topper, and K. Petermann, "Design Concept for Singlemode Polymer Waveguides", *Electronics Letters*, Vol. 32, pages 212–313 (1996); Robitaille et al., "Design and Fabrication of Low-Loss Polymer Waveguide Components for On-Chip Optical Interconnection", *IEEE Photonics Technology Letters* 8 (1996) 1647–1649. A similar process of interferometer development has been described by Levenson et al. of France Telecom (Levenson et al., "Advances in Organic Polymer-Based Optoelectronics", In ACS Symposium Series 601, *Polymers for Second Order Nonlinear Optics*, G. A. Lindsay and K. D. Singer, eds., (Washington, D.C.: American Chemical Society, 1995)).

Polymer waveguides have been fabricated in a number of ways: reactive ion etching (RIE), pbotobleaching and photocrosslinking etc. While RIE is the most widely used because of established techniques in the semiconductor industry, one of the simplest ways to fabricate a waveguide according to the invention is by photobleaching (as described in the Example which follows), although any other appropriate means (particularly those described in the application entitled "A Multi-Functional Optical Switch (Optical Wavelength Division Multiplexer/Demultiplexer, Add-Drop Multiplexer and Inter-Connect Device) And Its Method of Manufacture", U.S. Ser. No. 09/357,201, filed Jul. 20, 1999 by Alireza Gharavi as Case Number 98,468-A and Express Mail Number EM366141421U.S., incorporated by reference) can be employed. This photobleaching method (as well as other methods) optimally is employed to fabricate waveguides, for instance, having the arrangement depicted in FIG. 5.

For the case in FIG. 5 where $n_1$ is very much less than $n_3$, e.g., $n_1$ is 1, and $n_3$ is 1.5 or greater (i.e., an asymmetric waveguide), the required refractive indices have the relationship in refractive index difference ($\Delta n$):

$$\Delta n = n_2 - n_3 \geq (2m_s+1)^2 \lambda_o^2 / (32 n_2 t^2)$$

where t is the thickness of the waveguide, $\lambda_o$ is the vacuum wavelength and $m_s$ is the propagation mode, or guided wave mode) Hunsperger, "Integrated Optics: Theory and Technology", Third Edition, Springer-Verlag, New York. While $m_s=0$ is preferred according to the invention (lowest mode), higher modes are possible depending on structure, with $m_s=x$, where x is any whole number from 1 to infinity, and desirably, is any whole number from 1 to 10, especially from 1 to 4. Therefore for an asymmetric 3 $\mu$m thick sample at 1.3 $\mu$m wavelength, $\Delta n=0.003$ will suffice for single mode ($m_s=0$) confinement. This condition can be satisfied by photo-induced birefringence laser writing (e.g., Rochon et al. (1992), supra; Kim et al., supra). Increasing the waveguide thickness requires an even smaller $\Delta n$ to satisfy the beam confinement condition.

Thus, for an asymmetric waveguide as depicted in FIG. 5, desirably $n_1<n_2$ and $n_3$ is $<n_2$. In FIG. 5, light is carried in the $n_2$ layer (i.e., the $n_2$ layer functions as the waveguide), for this to happen, the index of refraction $n_3$ and $n_1$ must be less than the index of refraction $n_2$.

For the case where $n_3=n1$ (i.e., a symmetric waveguide), for waveguiding of a given mode to occur, the following index condition must be satisfied:

$$\Delta n = (n_2 - n_1) \geq \frac{m_s^2 \lambda_o^2}{4 t^2 (n_2 + n_1)}$$

where t, $\lambda_o$, and $m_s$ are as previously described. This condition for $\Delta n$ in the case of a symmetric waveguide is easily satisfied by the smallest difference between $n_1$ and $n_2$, a difference which clearly lies within the laser-induced birefringence limits (Yu et al., "Highly Stable Copolyimides for Second Order Nonlinear Optics; *Macromolecules*; 29, pages 6139–6142 (1996); Gharavi et al., "Fine-Tuning Optical Nonlinearity and Thermal Stability in Functionalized Co-polyimides", (presentation), *American Physical Society Meeting*, Mar. 18–22 (1996)).

EXAMPLE 5

Waveguide fabrication and Photo-bleaching

In the context of these constraints discussed in Example 4, it is possible to fabricate waveguides by simple photobleaching. Such photobleaching has been successfully implemented for other polymer structures (Keil, supra; Rikken et al., "Poled Polymers for Frequency Doubling of Diode Lasers", *Proc. SPIE* 1337 (1990) 35). Thus, this Example describes the use of photobleaching in waveguide fabrication according to the invention.

According to the method, desired refractive indices can be carefully adjusted by adjusting the photobleaching rate. The destruction of the chromophores by photobleaching, using a photo-masking technique that causes photo-dissociation if chromophores in the material produces efficient waveguides. Other techniques such as reactive ion etching (RIE) have also been used for fabricating waveguides (Ziari et al., "Polymer Electro-optic Waveguide Fabrication", In *Polymers for Second-Order Nonlinear Optics*, G. A. Lindsay and K. D. Singer, eds., ACS Symposium Series 601, (Washington, D.C.: American Chemical Society, 1995)).

This process of photobleaching is depicted in FIG. 13. Typically, a metallic mask (e.g., chromium coated quartz mask, (150)) is made by patterning the shape of the waveguide on a Cr-metal coated thin quartz slide using an etching technique, e.g., photolithography or excimer laser ablation. The mask also can be obtained commercially (Metrigraphics, Division of Dynamics Research Corporation, Wilmington, Mass. 01887). This mask is then placed on the surface of the polyimide film or other appropriate polymeric material (50), and irradiation (80) is carried out using ultraviolet light from a laser source such as a mercury lamp or a nitrogen or excimer laser.

The waveguide is protected from UV radiation by the patterning on the mask, such that the chromophores are preserved in the region of the waveguide alone (90), and are destroyed outside the region of the waveguide (100). This causes a higher refractive index and thickness in the waveguide than in the UV-exposed regions of the polymer film (see, e.g., Ito et al., supra, Lindsay et al., supra, Edelman et al., supra). What results from this process is an unbleached waveguide (90), and bleached polymer (100) in the area surrounding the waveguide.

Photobleaching magnitude is a function of depth and produces a waveguide that can be modeled as a ridge waveguide (Otomo et al., "Second Harmonic Generation by Counter-Directed Guided Waves in Poled Polymer Waveguides", In *Polymers for Second Order Nonlinear Optics*, ACS Symposium Series 601 (Washington, D.C.: American Chemical Society, 1995) 469–483).

Accordingly, this Example provides the use of photobleaching in device fabrication according to the invention.

EXAMPLE 6

Waveguide Fabrication and Light Coupling

This example describes coupling techniques according to the invention.

A prism coupler is frequently used for input or output coupling of signal into the waveguide layers. Each coupled mode is launched at a specific incident angle. It therefore is possible to launch a specific guided mode in the waveguide, and each guided mode will exit at a specific angle. Alternately, light coupling can be performed by attaching a pig-tail laser diode to the waveguide. Using an excimer laser, a wedge with micrometer dimensions can be easily etched into polymeric substrates, which then serves as the attachment site of the diode.

This method thus provides the use of prisms in coupling techniques that advantageously can be employed in the invention.

EXAMPLE 7

Device Testing and Solute/Solvent Interference

This Example discussing means of distinguishing between background index changes.

In certain instances with use of the invention, there can be possible difficulty in distinguishing between background index changes—i.e., changes in the waveguide due to solvent and other solutes that are of no interest vis-à-vis the analytical problem. To overcome this problem, desirably all other signals are isolated from that of the target analyte. This can be accomplished by a variety of means, including but not limited to, use of a double interferometer, for instance, having the design shown in FIGS. 15A–B.

According to this method, two interferometers are fabricated side-by-side on the same glass substrate. The Sensor Area of the device is made up of two parallel waveguides with the sensor arm of one modified by the receptor/catalyst of choice (i.e., the "bio-activated arm"), and the other (i.e., the "reference arm") left untreated. When a sample solution is applied to both arms in the Sensor Area, the modified sensor arm alone will be affected by the analyte molecule, and perhaps also by the solvent. The solvent effect, if any, will be detected solely by the reference arm. Subtraction of the two signals (i.e., resulting from the reference arm in each of the interferometers) then removes the artifactual interference arising from the solvent.

All of the references cited herein are hereby incorporated in their entireties by reference In particular, the application entitled "A Multi-Functional Optical Switch (Optical Wavelength Division Multiplexer/Demultiplexer, Add-Drop Multiplexer and Inter-Connect Device) And Its Method of Manufacture", U.S Ser. No. 09/357,201, filed Jul. 20, 1999 by Alireza Gharavi as Case Number 98,468-A and Express Mail Number EM366141421US is incorporated herein in its entirety by reference, and provides additional detail (e.g., on 2°-NLO polymers for use in optical devices, waveguide design and synthesis, and the like.)

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A waveguide sensing device for detecting or measuring the amount of analyte present in a sample, wherein said device comprises:
   (a) a sensor arm comprising a site for sample addition that has been modified with an analyte binding partner, and having a first end in optical communication with a second end;
   (b) a modulator arm comprising a site for application of an electric field and having a first end in optical communication with a second end;
   (c) a means for applying an electric field to said modulator arm;
   (d) an input port connected to said first end of each of said sensor arm and said modulator arm, that provides a means for directing an optical signal to each of said first ends; and
   (e) an output port connected to said second end of each of said sensor arm and said modulator arm, that provides a means for combining the optical signal received from each of said second ends and directing the combined signal to a detector,
      wherein said modulator arm and sensor arm are each comprised of an optical nonlinear second-order polymer.

2. The device of claim 1, wherein said modification with an analyte binding partner is covalent.

3. The device of claim 1, wherein said modification with an analyte binding partner is non-covalent.

4. The device of claim 1, wherein said optical nonlinear second-order polymer comprising said sensor arm is present as a film having a surface and an interior, and said modification with an analyte binding partner is by association of said analyte binding partner with said surface.

5. The device of claim 1, wherein said optical nonlinear second-order polymer comprising said sensor arm is present as a film having a surface and an interior, and said modification with an analyte binding partner is by association of said analyte binding partner with said surface and said interior.

6. The device of claim 1, wherein said optical nonlinear second-order polymer comprises a chromophore selected from the group consisting of sulfone diazo, dialkyl amino nitro azo, and dialkyl amino nitro diazo.

7. The device of claim 1, wherein said optical nonlinear second-order polymer comprises a chromophore selected from the group consisting of

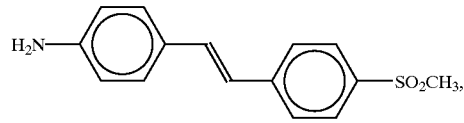

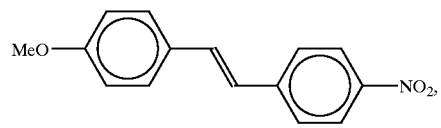

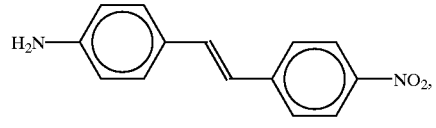

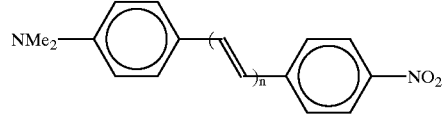

wherein n is 2, 3, or 4,

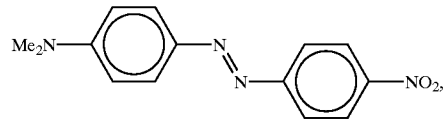

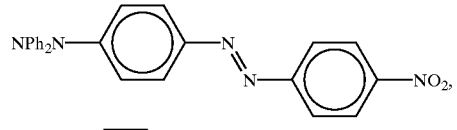

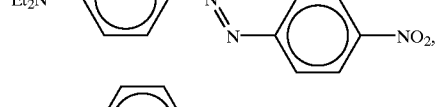

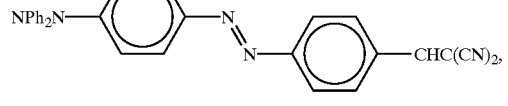

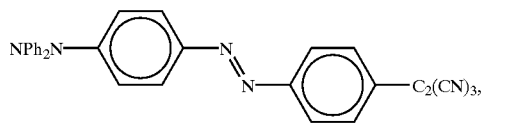

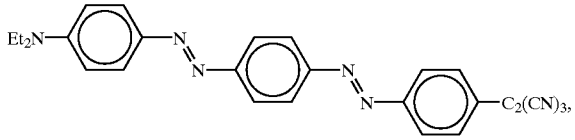

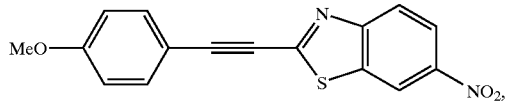

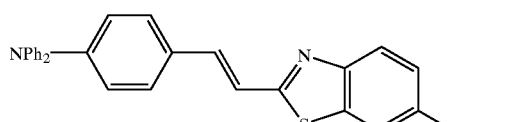, and

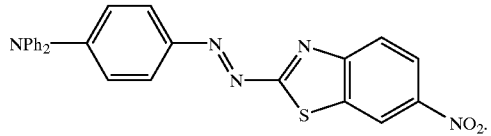.

8. The device of claim 1, wherein said analyte binding partner is selected from the group consisting of an ion-selective macrocycle, a broadly-selective cyclo-oligosaccharide, and metabolite-selective receptors/enzymes.

9. The device of claim 1, wherein said analyte binding partner is selected from the a group consisting of Hancock cryptand, (+)mephobarbital-selective β-D-cyclodextrin, and glucose oxidase/avidin conjugate.

10. A method of detecting an analyte, said method comprising:
    (a) obtaining a waveguide sensing device according to claim 1,
    (b) applying an optical signal to said input port;
    (c) applying an electric field to said modulator arm;
    (d) contacting said sensor arm with a sample that does not contain analyte and assessing said optical signal from said output port;
    (e) contacting said sensor arm with a sample to be tested for the presence of analyte and assessing said optical signal from said output port; and
    (f) comparing the optical signal assessed from said output port upon contacting with a sample to be tested for the presence of analyte relative to the signal assessed upon contacting with a sample that does not contain analyte, with any difference being due to the presence of said analyte.

11. The method of claim 10, wherein the amount of said analyte is determined by the rate of change of the optical signal assessed from said output port with addition of said sample to be tested for the presence of analyte as compared to with addition of said sample that does not contain analyte.

12. A waveguide sensing device for detecting or measuring the amount of analyte present in a sample, wherein said device comprises:

(a) a first and second sensor arm, each comprising a site for sample addition and having a first end in optical communication with a second end, and only one of which has been modified with an analyte binding partner so as to comprise the bioactivated arm, the other comprising a reference arm;

(b) a first and second modulator arm, each comprising a site for application of an electric field and having a first end in optical communication with a second end;

(c) a means for applying an electric field to said first modulator arm;

(d) a means for applying an electric field to said second modulator arm;

(e) a first input port connected to said first end of each of said first sensor arm and said first modulator arm, that provides a means for directing an optical signal to each of said first ends of said first sensor arm and said first modulator arm;

(f) a second input port connected to said first end of each of said second sensor arm and said second modulator arm, that provides a means for directing an optical signal to each of said first ends of said second sensor arm and said second modulator arm;

(g) a first output port connected to said second end of each of said first sensor arm and said first modulator arm, that provides a means for combining the optical signal received from each of said second end of each of said first sensor arm and said first modulator arm and directing the combined signal to a detector; and (h) a second output port connected to said second end of each of said second sensor arm and said second modulator arm, that provides a means for combining the optical signal received from each of said second end of each of said second sensor arm and said second modulator arm and directing the combined signal to a detector;

wherein said first and second modulator arm and first and second sensor arm, are each comprised of an optical nonlinear second-order polymer.

13. The device of claim 12, wherein said modification with an analyte binding partner is covalent.

14. The device of claim 12, wherein said modification with an analyte binding partner is non-covalent.

15. The device of claim 12, wherein said optical nonlinear second-order polymer comprising said bioactivated arm is present as a film having a surface and an interior, and said modification with an analyte binding partner is by association of said analyte binding partner with said surface.

16. The device of claim 12, wherein said optical nonlinear second-order polymer comprising said bioactivated arm is present as a film having a surface and an interior, and said modification with an analyte binding partner is by association of said analyte binding partner with said surface and said interior.

17. The device of claim 12, wherein said optical nonlinear second-order polymer comprises a chromophore selected from the group consisting of sulfone diazo, diallyl amino nitro azo, and dialkyl amino nitro diazo.

18. The device of claim 12, wherein said optical nonlinear second-order polymer comprises a chromophore selected from the group consisting of

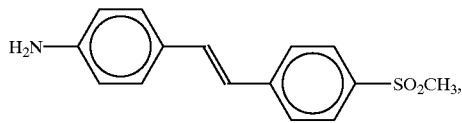

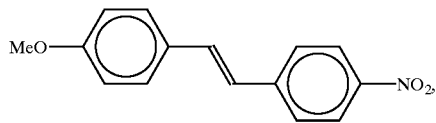

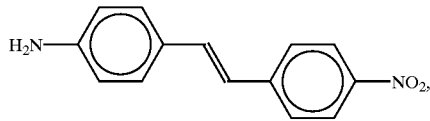

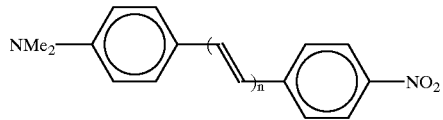

wherein n is 2, 3, or 4,

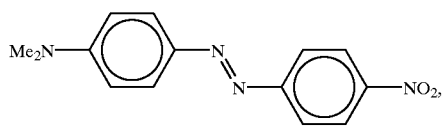

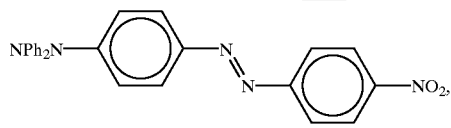

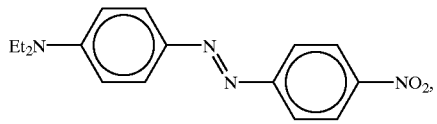

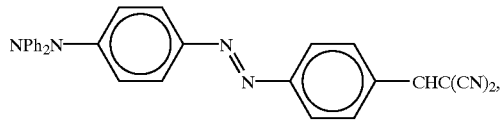

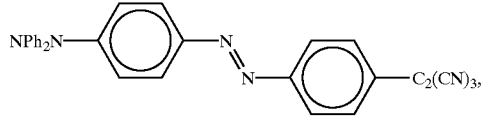

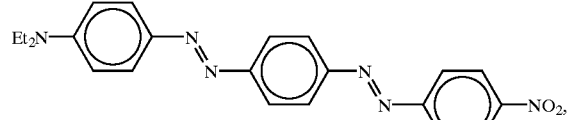

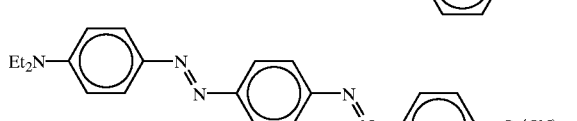

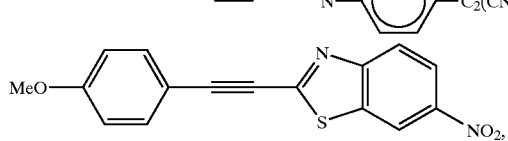

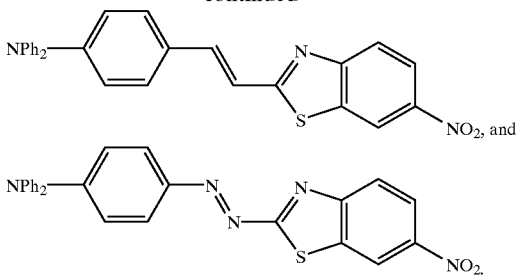

19. The device of claim 12, wherein said analyte binding partner is selected from the group consisting of an ion-selective macrocycle, a broadly-selective cyclo-oligosaccharide, and metabolite-selective receptors/enzymes.

20. The device of claim 12, wherein said analyte binding partner is selected from the group consisting of Hancock cryptand, (+)-mephobarbital-selective β-D-cyclodextrin, and glucose oxidase/avidin conjugate.

21. A method of detecting an analyte, said method comprising:

(a) obtaining a waveguide sensing device according to claim 12, (b) applying an optical signal to said first and second input port;

(c) applying an electric field to said first and second modulator arm;

(d) contacting said first and second sensor arm with a sample to be tested for the presence of analyte;

(e) assessing the optical signal from said first and second output port; and (f) comparing the optical signal assessed from said first output port relative to the signal assessed from said second output port, with any difference being due to the presence of said analyte.

22. The method of claim 21, wherein said method provides for subtraction of solvent effect.

* * * * *

UNITED STATES PATENT AND TRADEMARK OFFICE
CERTIFICATE OF CORRECTION

PATENT NO.    : 6,429,023 B1
DATED         : August 6, 2002
INVENTOR(S)   : Alireza Gharavi It is certified that error appears in the above-identified patent and that said Letters Patent is hereby corrected as shown below:

<u>Column 31,</u>
Line 63, please replace "diallyl amino" with -- dialkyl amino --.

Signed and Sealed this

Fourth Day of March, 2003

JAMES E. ROGAN
*Director of the United States Patent and Trademark Office*